United States Patent
Hide et al.

(10) Patent No.: US 8,546,542 B2
(45) Date of Patent: Oct. 1, 2013

(54) ANTI-SWEAT ANTIGEN MONOCLONAL ANTIBODY

(75) Inventors: Michihiro Hide, Hiroshima (JP); Toshihiko Tanaka, Hiroshima (JP); Kaori Ishii, Hiroshima (JP); Hidenori Suzuki, Hiroshima (JP)

(73) Assignee: Hiroshima University, Higashi-Hiroshima-Shi, Hiroshima-Ken (JP)

(*) Notice: Subject to any disclaimer, the term of this patent is extended or adjusted under 35 U.S.C. 154(b) by 0 days.

(21) Appl. No.: 12/990,775

(22) PCT Filed: May 1, 2009

(86) PCT No.: PCT/JP2009/058571
§ 371 (c)(1), (2), (4) Date: Jan. 14, 2011

(87) PCT Pub. No.: WO2009/133951
PCT Pub. Date: Nov. 5, 2009

(65) Prior Publication Data
US 2011/0117103 A1 May 19, 2011

(30) Foreign Application Priority Data
May 2, 2008 (JP) ................ 2008-120680
Dec. 26, 2008 (JP) ................ 2008-334562

(51) Int. Cl.
*C07K 16/00* (2006.01)
*A61K 39/395* (2006.01)
*C12N 5/12* (2006.01)

(52) U.S. Cl.
USPC ............... 530/387.1; 530/388.1; 530/388.85; 424/139.1; 424/141.1; 435/326; 435/346; 435/7.1

(58) Field of Classification Search
None
See application file for complete search history.

(56) References Cited

U.S. PATENT DOCUMENTS
2006/0134706 A1* 6/2006 Hide et al. ............... 435/7.2

FOREIGN PATENT DOCUMENTS
| JP | 2008-69118 | 3/2008 |
| WO | WO03/084991 A1 | 10/2003 |
| WO | WO2005/005474 A1 | 1/2005 |
| WO | WO-2008131302 A2 | 10/2008 |

OTHER PUBLICATIONS

Bieber, "Atopic dermatitis" NEJM, 385, (2008) 14, 1483-1494.*
Nelson et al. "Monoclonal Antibodies" J Clin Pathol: Mol Pathol (2000), 53, 111-117.*
Shiohara et al. "Defective sweating responses in atopic dermatitis" Curr Probl Dermatol., 41 (2011), 68-79.*
Kato et al., "CystatinA Inhibits IL-8 Production by Keratinocytes Stimulated with Der p 1 and Der f 1: Biochemical Skin Barrier Against Mite Cysteine Proteases," *J. Allergy Clin. Immunol.* 116(1): 169-176 (2005).
Seguchi, "Abnormalities in Epidermal Terminal Differentiation Products in Skin from Patients with Atopic Dermatitis," *Medical Journal of Kinki University* 18(4): 511-519 (1993). (English abstract).
English Translation of International Preliminary Report on Patentability for International Application No. PCT/JP2009/058571, mailed Dec. 29, 2010.
International Search Report for International Application No. PCT/JP2009/058571, dated May 25, 2009 (date of completion of report) and Jun. 2, 2009 (dated of mailing of report).
Tanaka et al., "Semi-purification of the immunoglobulin E-sweat antigen acting on mast cells and basophils in atopic dermatitis," *Experimental Dermatology* 15:283-290 (2006).
Extended European Search Report for European Application No. EP 09 73 8888, mailed Sep. 27, 2011.
Hide et al., "IgE-Mediated Hypersensitivity Against Human Sweat Antigen in Patients with Atopic Dermatitis," *Acta. Derm. Venereol.* 82:335-340 (2002).
Hide et al., "Ase Ni Taisuru I-Kei 'Allergy' to Atopiisei Hifuen," *Hakkangaku* 14(1):18-22 (2007) (English Language Translation of Figures 1-5 Only).
Tanaka et al., "Atopiisei Hifuen Kanja No Ase Ni Taisuru I-Kei 'Allergy' Hannou," *Arerugi* 49(9/10): 902 (2000) (English Language Translation provided).
Tanaka et al., "Atopiisei Hifun Kanja Ase No Naka No Jikou Kougen No Kaiseki," *Japanese Journal of Dermatology* 113(5): 726 (2003) (English Language Translation provided).
Tanaka et al., "Atopiisei Hifukuen Kanja Ni Okeru Ase 'Allergy' Ni Tsuite No Kenkyuu," *Hiroshima Igaku* 61(1):47 (2008) (English Language Translation provided).
Vrtala et al., "Immunization with purified natural and recombinant allergens induces mouse IgG1 antibodies that recognize similar epitopes as human IgE and inhibit the human IgE-allergen interaction and allergen-induced basophil degranulation," *J. Immunol.* 160:6137-6144 (1998).
Notification of Reason for Rejection for Japanese Patent Application No. 2010-510175, mailed Jul. 12, 2013 (14 pages).

* cited by examiner

*Primary Examiner* — Daniel E Kolker
*Assistant Examiner* — James Rogers
(74) *Attorney, Agent, or Firm* — Clark & Elbing LLP

(57) ABSTRACT

The invention relates to an antibody that inhibits histamine releasing activity induced by an antigenic substance contained in sweat. The invention further relates to an antibody which can react with a sweat antigen composition and inhibit the histamine releasing activity of the composition on a sweat antigen stimulation-responsive cell.

29 Claims, 14 Drawing Sheets

ANTI-SWEAT ANTIGEN MONOCLONAL ANTIBODY

CROSS-REFERENCE TO RELATED APPLICATIONS

This application is the U.S. national stage filing under 35 U.S.C. §371 of international application PCT/JP2009/058571, filed May 1, 2009, which claims benefit of Japanese Patent Application JP 2008-120680 filed May 2, 2008, and Japanese Patent Application JP 2008-334562, filed Dec. 26, 2008.

TECHNICAL FIELD

The present invention relates to a monoclonal antibody against a sweat antigen composition. The present invention also relates to a determination method using the antibody, and a pharmaceutical composition and a diagnosis agent or kit comprising the antibody. The present invention further relates to a hybridoma capable of producing the antibody and a method of screening for or producing the hybridoma.

BACKGROUND ART

In recent years, the number of atopic dermatitis patients has been increasing drastically. With the ratio of atopic dermatitis patients exceeding 30% of dermatological patients, atopic dermatitis is a predominant skin disease. Atopic dermatitis is an atopic disease that is caused by genetic factors more likely to produce IgE antibodies against usual antigens, plus various environmental factors. This disease develops in infancy, takes a chronic course with aging, and mostly remits before adolescence. However, some cases persist even after adolescence or develop after adolescence. Most cases in adults are particularly intractable, and remission is hardly expected as they are more aged. The established lesions are lichenified with serious and often spasmodic itching, resulting in frequent exacerbations and remissions with certain association with other atopic diseases.

Much remains to be revealed about a mechanism underlying the development of such atopic dermatitis. There is also a problem with discrimination from other skin diseases. Thus, a treatment method thereof has not been established yet. Attempts have previously been made, such as the external use of adrenal corticosteroids, the medication of an antihistaminic agent or chemical transmitter release inhibitor, or diet therapy in which egg, milk, soybeans, and so on are removed from food materials, the removal of antigenic substances such as mites and fungi (molds) from living environments, etc. However, the medication still faces a problem in adverse reaction, because the drug is used in children in their growing years, furthermore over a long period. Moreover, the diet therapy or the measure to remove environmental antigens has the difficulty in completely removing antigens and has the problem that mental burden is also great.

In light of such circumstances, studies have been conducted recently to elucidate a mechanism underlying the development of atopic dermatitis by making full use of molecular biological findings, while enhancing therapeutic effect by inhibiting a portion of the development mechanism. For example, a method focusing on the fact that the production of IgE antibodies against antigens is partially responsible for the mechanism to cause symptoms, as described above, has been proposed, and this method involves alleviating symptoms by the external use of a substance inhibiting the production of IgE antibodies against antigens (Japanese Patent Laid-Open Publication Nos. 109290/1995, 109292/1995, and 100236/1997).

Meanwhile, it has previously been reported an antigenic substance that is contained in sweat and induces atopic dermatitis (WO 03/084991 A1; Japanese Patent No. 3983260; and the year 2002 Health Labour Sciences Research Grant, Research Report of Research on Allergic disease and immunology (First Part, p. 101-103, issued on March 2003 by the Japanese Ministry of Health, Labour and Welfare)). However, neither has this antigenic substance been identified, nor an antibody that inhibits the histamine releasing activity of the antigenic substance has been reported.

SUMMARY OF THE INVENTION

The present inventors had attempted so far to obtain antibodies using a composition prepared from human sweat, but failed to obtain an antibody that binds to a histamine release activating substance contained in human sweat and inhibits histamine release from basophiles, mast cells, or the like.

Thus, the present inventors have prepared a monoclonal antibody by screening a hybridoma using, as an index, an amount of histamine release from basophiles, using, as an antigen, a pass-through fraction (anti-human cystatin A antibody-non-adsorbed fraction) obtained by: obtaining a fraction contained in secretions from a human sweat gland using, as an index, histamine releasing activity; and further subjecting the fraction to anti-human cystatin A antibody affinity chromatography. The present inventors have consequently found that: the monoclonal antibody inhibits sweat antigen fraction-induced histamine release from the basophiles of atopic dermatitis patients (Example 2 and 6-4 (3) of Example 6); a sweat antigen composition can be collected by using the antibody (3-1 of Example 3); a sweat antigen fraction can be detected by using the antibody (3-2 and 3-3 of Example 3 and Example 7); sweat antigen-specific IgE antibodies in atopic dermatitis patient's serum can be detected by using the antibody (Examples 4 and 5); and sweat antigen-specific IgE antibodies in cholinergic urticaria patient's serum can be detected by using the antibody (Example 8). The present invention is based on these findings.

An object of the present invention is to provide a monoclonal antibody which can inhibit histamine release, induced by a sweat antigenic substance, from a sweat antigen stimulation-responsive cell. Another object of the present invention is to provide a determination method using the antibody, and a pharmaceutical composition and a diagnosis agent or kit comprising the antibody. A further object of the present invention is to provide a hybridoma which can produce the antibody and a method of screening or producing the hybridoma.

According to the present invention, there is provided an antibody or a functional fragment thereof which can react with a sweat antigen composition and inhibit histamine release, induced by the composition, from a sweat antigen stimulation-responsive cell (hereinafter, referred to as an "antibody of the first aspect according to the present invention").

According to the present invention, there is provided an antibody or a functional fragment thereof which reacts with a sweat antigen reacting through antigen-antibody reaction with the antibody of the first aspect according to the present invention (hereinafter, referred to as an "antibody of the second aspect according to the present invention") (hereinafter, the "antibody of the first aspect according to the present invention" and the "antibody of the second aspect according to the present invention" are together referred to as an "antibody according to the present invention").

According to the present invention, there is provided a method of determining a sweat antigen-associated disease or a risk of development thereof, comprising detecting a sweat antigen and/or a sweat antigen-specific IgE antibody in a test sample using the antibody of the first aspect according to the present invention (hereinafter, referred to as an "determination method according to the present invention").

According to the present invention, there is provided a pharmaceutical composition for use in the prevention or treatment of a sweat antigen-associated disease, comprising the antibody according to the present invention and optionally one or more pharmaceutically acceptable carrier and/or diluent.

According to the present invention, there is provided use of the antibody according to the present invention for the production of a preventive or therapeutic agent for a sweat antigen-associated disease.

According to the present invention, there is provided a method of preventing or treating a sweat antigen-associated disease, comprising administering a preventively or therapeutically effective amount of the antibody according to the present invention to a mammal including a human.

According to the present invention, there is provided an agent or kit of diagnosing a sweat antigen-associated disease or a risk of development thereof, comprising the antibody of the first aspect according to the present invention and/or the antibody of the second aspect according to the present invention.

According to the present invention, there is provided a hybridoma for use in the production of an antibody or a functional fragment thereof which can react with a sweat antigen composition and inhibit histamine release, induced by the composition, from a sweat antigen stimulation-responsive cell, which is the hybridoma producing a sweat antigen-specific antibody, obtained by selection using, as an index, an amount of histamine release from the sweat antigen stimulation-responsive cell (hereinafter, referred to as a "hybridoma of the first aspect according to the present invention").

According to the present invention, there is provided a hybridoma for use in the production of an antibody or a functional fragment thereof that can be combined with the antibody of the first aspect according to the present invention to detect a sweat antigen composition by a sandwich method (hereinafter, referred to as a "hybridoma of the second aspect according to the present invention").

According to the present invention, there is provided a method of screening for a hybridoma producing a sweat antigen-specific antibody, comprising selecting a hybridoma producing an antibody having histamine release inhibiting effect, using, as an index, an amount of histamine release from a sweat antigen stimulation-responsive cell.

According to the present invention, there is provided a method of producing a hybridoma producing a sweat antigen-specific antibody, comprising:
(i) selecting a hybridoma producing an antibody having histamine release inhibiting effect, using, as an index, an amount of histamine release from a sweat antigen stimulation-responsive cell; and
(ii) cloning the hybridoma obtained in (i).

The antibody according to the present invention which can recognize a sweat antigen composition with specificity and sensitivity and as such, can be used advantageously as an assay reagent for a sweat antigen, a diagnosis agent, or the like. The antibody according to the present invention can also be immobilized, for use, on a solid phase such as a plate and as such, advantageously allows highly sensitive detection of a sweat antigen or a sweat antigen-specific IgE antibody using a sandwich method or the like. The determination method according to the present invention can perform the diagnosis of a sweat antigen-associated disease using patient's serum, without conducting intracutaneous reaction test, prick test, or the like using patient's own skin or histamine release test using patient's blood cells, and as such, is advantageously convenient. The determination method according to the present invention can also advantageously perform the diagnosis of a sweat antigen-associated disease even relative to a patient (nonresponder) that cannot be determined by histamine release test conventionally used in the diagnosis of allergic diseases (atopic dermatitis, cholinergic urticaria, etc.).

Moreover, the antibody according to the present invention can inhibit histamine release from a sweat antigen stimulation-responsive cell and as such, can also be used advantageously as a preventive or therapeutic drug for a sweat antigen-associated disease.

BRIEF DESCRIPTION OF THE DRAWINGS

FIG. 4-1 is a diagram showing results of western blot (native polyacrylamide gel (NON-SDS-PAGE mini (4 to 20 w/v %) gel) using monoclonal antibodies obtained in Example 2.

FIG. 4-2 is a diagram showing results of western blot (native-PAGE gel, PAGEL NPU-15L (15 w/v %) gel) using monoclonal antibodies obtained in Example 2.

FIG. 4-3 is a diagram showing results of electrophoresis.

FIG. 4-4 is a diagram showing results of histamine release test of fractions 1 to 3.

FIG. 12-1 is a diagram showing results of sandwich ELISA test using monoclonal antibodies obtained in the present invention and smith-2.

FIG. 12-2 is a diagram showing a calibration curve for QRX assay using the same sandwich ELISA as above.

DETAILED DESCRIPTION OF THE INVENTION

[Sweat Antigen Composition]

Figure 1:
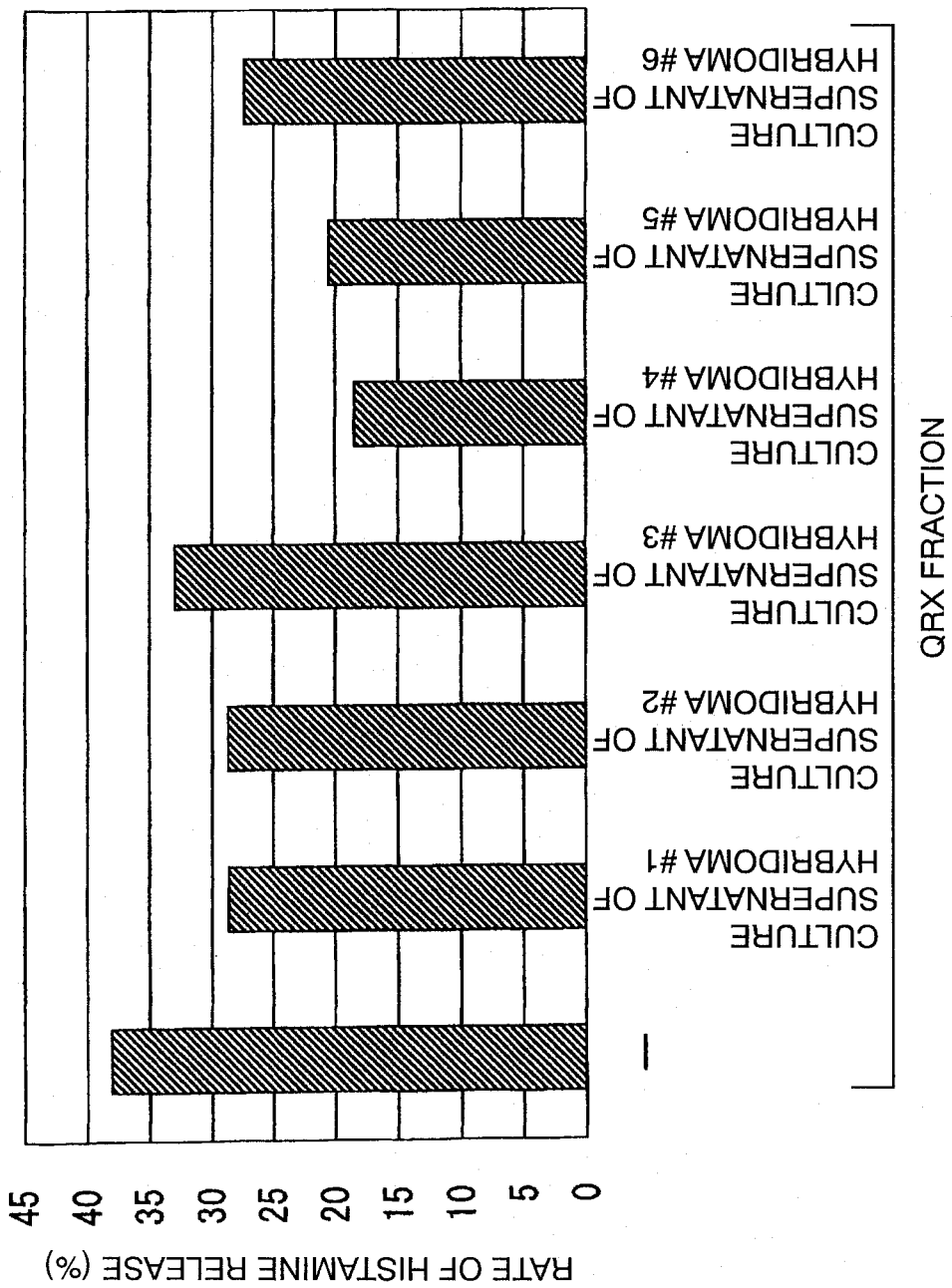
FIG. 1 is a diagram showing results of histamine release test using hybridoma culture supernatants.

Human sweat contains an antigenic substance (hereinafter, also referred to as a "sweat antigen") that induces allergic reaction and causes diseases such as atopic dermatitis and cholinergic urticaria. The sweat antigen is contained not only in sweat derived from these patients but also in sweat derived from healthy individuals.

In the present specification, a "sweat antigen composition" means a composition comprising the sweat antigen.

According to the present invention, the sweat antigen composition can be used in the preparation of an antibody according to the present invention.

The sweat antigen composition can be obtained by separating a fraction with histamine releasing activity from secretions from a human sweat gland. The obtained fraction with histamine releasing activity is further subjected to anti-human cystatin A antibody affinity chromatography, and a pass-through fraction (i.e., anti-human cystatin A antibody-non-adsorbed fraction) may be selected.

The "secretions from a sweat gland" are sweat or proteins, sugars, lipids, or nucleic acids contained in sweat or their complexes and can be obtained from the skin of the face, head and neck area, trunk, upper limb, or the like. Moreover, the secretions can also be obtained from saliva, lacrimal fluid, or urine.

The collected secretions can be used directly as the "secretions from a sweat gland". Preferably, filtrates or the like obtained by removing insoluble matter can be used.

Examples of the method of removing insoluble matter include filter filtration and centrifugation. Filter filtration is preferable.

The "fraction with histamine releasing activity" means a fraction containing the antigenic substance that induces histamine release from a sweat antigen stimulation-responsive cell. This fraction can be obtained by separating secretions from a sweat gland using anion-exchange column chromatography, reverse-phase column chromatography, and gel filtration chromatography and selecting a fraction having histamine releasing activity.

The "sweat antigen stimulation-responsive cell" is a cell expressing IgE receptors on its surface and needs only to be a cell capable of secreting chemical transmitters such as histamine through activation by sweat antigen caused by the binding of sweat antigen to IgE antibodies bound to the IgE receptors. Examples thereof include basophiles, mast cells, and cell strains capable of releasing chemical transmitters such as histamine, which are artificially prepared by the expression of IgE receptor genes. Basophiles are preferable.

The separation method may be any chromatography known in the art without particular limitations. Examples thereof include anion-exchange column chromatography, reverse-phase column chromatography, gel filtration chromatography, and electrophoretic techniques, and combinations of two or more thereof.

Examples of the anion-exchange column chromatography include commercially available anion-exchange columns such as MonoQ 10/100 GT (GE Healthcare Biosciences).

Examples of the reverse-phase column chromatography include commercially available reverse-phase columns such as SOURCE 15 RPC ST 4.6/100 (GE Healthcare Biosciences).

Examples of the gel filtration chromatography include commercially available gels such as Superdex 75 PC 3.2/30 (GE Healthcare Biosciences).

Preferably, anion-exchange column chromatography, reverse-phase column chromatography, and gel filtration chromatography can be used in combination.

The "histamine releasing activity" can be determined according to a method known in the art. For example, the amount of histamine is measured, and a fraction can be determined as having histamine releasing activity, when the amount of free histamine with respect to the total amount of histamine falls within the range of 3 to 97% (Koro, O. et al., 3. Allergy Clin. Immunol., 103, 663-670, 1999).

The "anti-human cystatin A antibody affinity chromatography" can be performed according to a method described in, for example, Chromatography Handbook/Affinity Chromatography (GE Healthcare Biosciences).

An anti-human cystatin A antibody-immobilized carrier may be commercially available or may be prepared according to a method known in the art.

Preferably, the sweat antigen composition can bind to human's own IgE antibodies to activate a sweat antigen stimulation-responsive cell (e.g., mast cells or basophiles) such that the cell releases histamine. In addition, the sweat antigen composition is non-adsorbed onto the anti-human cystatin A antibody.

Preferably, the sweat antigen composition can be obtained by a method comprising:
(1) subjecting filter-filtered human sweat to anion-exchange column chromatography, then reverse-phase column chromatography, and finally gel filtration chromatography to obtain a fraction with histamine releasing activity; and
(2) subjecting the fraction with histamine releasing activity obtained in (1) to anti-human cystatin A antibody affinity chromatography.

The sweat antigen composition can be used in a preferable embodiment. For example, a substance which is migrated within an isoelectric point range of 4.5 to 4.8 in isoelectric focusing can be used. Alternatively, a substance which is migrated at a position of 35 kD to 100 kD with the position of marker protein migration as a guideline in electrophoresis using a native polyacrylamide gel can be used. Alternatively, a substance which is eluted at the second and third peak positions, more preferably at the second peak position, of three peaks with histamine releasing activity obtained by screening, in histamine release test using the basophiles of atopic dermatitis patients, a fraction obtained by anion-exchange chromatography can be used.

[Antibody]

An antibody of the first aspect according to the present invention can specifically recognize a sweat antigen composition contained in secretions from a human sweat gland and inhibit histamine release from a sweat antigen stimulation-responsive cell induced by a sweat antigen in a sweat allergy patient.

The antibody of the first aspect according to the present invention can be an antibody against a fraction with histamine releasing activity contained in secretions from a human sweat gland.

The antibody of the first aspect according to the present invention can be obtained by selecting a hybridoma using, as an index, an amount of histamine release from the sweat antigen stimulation-responsive cell.

An antibody of the second aspect according to the present invention can be an antibody that reacts through antigen-antibody reaction with a sweat antigen reacting through antigen-antibody reaction with the antibody of the first aspect according to the present invention.

In this context, the "antigen-antibody reaction" means the specific reaction of an antigen with its corresponding antibody selectively binding thereto.

The antibody of the second aspect according to the present invention can be obtained by selecting a hybridoma using a sandwich method using the antibody of the first aspect according to the present invention and a sweat antigen composition.

The antibody according to the present invention encompasses: a polyclonal or monoclonal antibody (also including a monoclonal antibody produced by a hybridoma producing the monoclonal antibody of the present invention) obtained by immunizing mammals such as mice with a sweat antigen composition; a chimeric antibody and humanized antibody produced using a gene recombination technique; and a human antibody produced using human antibody-producing transgenic animals or the like.

When the antibody according to the present invention is administered as a pharmaceutical drug to humans, a human antibody is preferable from the viewpoint of reduced adverse reaction.

The "human antibody" is an antibody of which regions are all derived from a human. The human antibody according to the present invention can be prepared using a method well known to those skilled in the art (see e.g., Epstein-Barr virus (EBV) immortalization method (Watson et al., 1983. J Immunol 130, 2442-2447), phage display method (Marks et al., 1991. J Mol Biol 222, 581-597; and Bardas et al., 1992. Proc Natl Acad Sci USA 89, 4457-4461), and complete human antibody-producing hybridoma method (Japanese Patent Laid-Open Publication No. 2007-000141)).

The "humanized antibody" is an antibody obtained by transplanting (CDR-grafting) only the gene sequence of an antigen-binding site (CDRs: complementarity determining regions) of a mouse antibody to a human antibody gene. The humanized antibody according to the present invention can be prepared using a method well known to those skilled in the art (see e.g., a method for producing a humanized antibody comprising CDRs (antigen-binding site) and some amino acid residues of FRs (framework regions) of a mouse antibody transplanted in a human antibody (Owens et al., 1994. J Immunol Methods 168, 149-165)).

The "chimeric antibody" is an antibody comprising variable regions of an antibody of certain species linked to constant regions of an antibody of species different therefrom. Specifically, the chimeric antibody can be prepared by: immunizing mice with antigens; excising sequences encoding antigen-binding antibody variable region (V regions) from the mouse monoclonal antibody gene; and binding them to antibody constant region (C region) genes derived from human bone marrows. The chimeric antibody according to the present invention can be prepared using a method well known to those skilled in the art (see e.g., Boulianne et al., 1984. Nature 312, 643-646; Morrison et al., 1984. Proc Natl Acad Sci USA 81, 6851-6855; Walls et al., 1993. Nucleic acid Research 21, 2921-2929; Norderhung et al., 1997. J Immunol Methods 204, 77-78; Persic et al., 1997. Gene 187, 9-18; and McLean et al., 2000. Mol Immunol 37, 837-845).

The monoclonal antibody according to the present invention can be prepared using a method well known to those skilled in the art. For example, the monoclonal antibody can be produced by hybridomas that are formed by the cell fusion between lymphocytes derived from mammals immunized with antigens and myeloma cells derived from mammals.

The sweat antigen composition described above can be used as an immunizing antigen. The antigen may be used as a complex with a carrier protein. The sweat antigen composition and the carrier protein can be bound chemically. The manner of chemical binding is not particularly limited, and covalent bond is preferable. Examples of the carrier protein include BSA and KLH. KLH is preferable.

The lymphocytes and the myeloma cells may be any of those derived from mammals without particular limitations. Examples of the mammals include pigs, cattle, mice, and rats. Mice are preferable.

The immunization can be performed by injecting immunizing antigens to the footpads of mammals. The injection method is not limited to this and may be hypodermic, intraperitoneal, or intravenous injection. The immunization is usually performed in several shots and preferably performed by administration together with an adjuvant. The adjuvant may be any of those expected to have adjuvant effect, such as alum, killed *Mycobacterium tuberculosis*, nucleic acids, a Freund's complete adjuvant, and a Freund's incomplete adjuvant, without limitations.

The cell fusion can be carried out according to a method known in the art (Nature, 256, 495 (1975)). For example, the cell fusion can be performed using lymphocytes obtained from the lymph nodes or spleens of the finally immunized mice and cells of tumor cell strain such as myeloma cells (usually, mouse BALB/c-derived P3-NS-1/1-Ag4-1, P3-X63-Ag8-U1 (P3U1), P3-X63-Ag8-653, SP2/0-Ag14, etc.).

The antibody-producing hybridoma can be obtained, for example, by performing selection and monocloning by methods exemplified below.

The antibody of the first aspect according to the present invention can react with a sweat antigen composition and inhibit histamine release from a sweat antigen stimulation-responsive cell induced by the composition. Thus, the selection of antibody-producing hybridomas can be performed by determining whether or not an antibody produced by a hybridoma can inhibit histamine release from the sweat antigen stimulation-responsive cell.

Whether or not the antibody can inhibit histamine release from the sweat antigen stimulation-responsive cell can be confirmed by measuring an amount of histamine release from the sweat antigen stimulation-responsive cell according to a method known in the art.

When the amount of histamine release in the presence of an antibody to be tested falls short of the amount of histamine release in the absence of the antibody, specifically, is 95% or lower, preferably 90%, more preferably 85%, even more preferably 80%, further preferably 75%, particularly preferably 70%, particularly more preferably 65%, most preferably 60% or lower thereof, the antibody can be determined as having inhibited histamine releasing activity.

The antibody of the second aspect according to the present invention can be combined with the antibody of the first aspect according to the present invention to detect a sweat antigen composition by a sandwich method. Thus, the selection of antibody-producing hybridomas can be performed by determining whether or not an antibody produced by a hybridoma can react through antigen-antibody reaction with a sweat antigen reacting through antigen-antibody reaction with the antibody of the first aspect according to the present invention.

Whether or not the antibody can react through antigen-antibody reaction with a sweat antigen reacting through antigen-antibody reaction with the antibody of the first aspect according to the present invention can be confirmed according to a method known in the art such as an immunological detection method based on a sandwich method.

When a signal level (e.g., fluorescence intensity or color intensity) obtained using an antibody to be tested in the immunological analysis method exceeds a signal level without the use of the antibody to be tested, specifically, is 1.1 times or more, preferably 1.5 times, more preferably 2 times or more the signal level, the antibody can be determined as reacting through antigen-antibody reaction with the sweat antigen reacting through antigen-antibody reaction with the antibody of the first aspect according to the present invention.

The selection of antibody-producing hybridomas can be performed by selecting hybridomas producing the antibody of interest reacting with a sweat antigen composition according to the present invention by various analysis methods (e.g., RIA, a plaque method, an agglutination reaction method, ELISA, flow cytometry, tissue staining, and western blotting) as secondary screening from cell culture supernatants containing actively growing hybridomas.

The obtained hybridomas may be cloned to obtain single clones.

Examples of the cloning method include FACS (Fluorescent Activated Cell Sorter) and a limiting dilution method generally often used. For example, the limiting dilution method is preferably performed such that the number of cells per well of a 96-well plate is one or less. Even if any of the methods are used, the cloning is preferably performed repetitively twice, preferably into single clones. The single clones thus obtained can be cultured by, for example, an in-vitro culture or in-vivo culture (growing as ascites) method to produce monoclonal antibodies.

The monoclonal antibodies can be purified using any method known in the art. For example, separation and purification can be performed from the obtained culture solution by appropriately combining general biochemical approaches such as salting out, ion exchange, gel filtration, affinity chromatography, and electrophoresis.

The antibody according to the present invention may be of any immunoglobulin class and subclass without particular limitations and is preferably IgM or IgG in immunoglobulin class. Furthermore, when the immunoglobulin class is IgG, its subclass is more preferably IgG2a or IgG1.

The polyclonal antibody according to the present invention can be prepared using a method well known to those skilled in the art. For example, the polyclonal antibody can be obtained from the serum of mammals immunized with antigens.

A "functional fragment" according to the present invention means a portion (partial fragment) of the antibody, which specifically recognizes a sweat antigen contained in secretions from a human sweat gland. Specific examples thereof include $F(ab')_2$ fragments, Fab fragments, single-chain variable fragments (scFvs), Diabodies, and Minibodies.

Preferable examples of the antibody of the first aspect according to the present invention include a monoclonal antibody (smith-1 antibody) produced by a hybridoma deposited under FERM BP-11110, a monoclonal antibody (smith-2 antibody) produced by a hybridoma deposited under FERM BP-11111, and a monoclonal antibody (smith-8 antibody) produced by a hybridoma deposited under accession No. FERM BP-11112.

Preferable examples of the antibody of the second aspect according to the present invention include a monoclonal antibody (adam-1 antibody) produced by a hybridoma deposited under accession No. FERM BP-11113.

The antibody according to the present invention is preferably a monoclonal antibody.

[Determination Method]

The antibody according to the present invention can be used in detecting a sweat antigen and/or a sweat antigen-specific IgE antibody. Thus, according to the present invention, a sweat antigen-associated disease or a risk of development thereof can be determined by detecting a sweat antigen and/or a sweat antigen-specific IgE antibody in a test sample using the antibody according to the present invention.

In this context, the phrase "determining a sweat antigen-associated disease" means determining whether or not a subject displaying symptoms (signs) of the sweat antigen-associated disease is affected with this disease caused by the sweat antigen.

Moreover, the phrase "determining a risk of developing the sweat antigen-associated disease" means determining whether or not a subject displaying no symptoms (signs) of the sweat antigen-associated disease has a risk of developing the sweat antigen-associated disease.

The presence of a sweat antigen in a biological sample serves as an index of a sweat antigen-associated disease or a risk of development thereof (particularly, an index of a risk of developing the sweat antigen-associated disease). According to Examples 3, 6, and 7, it was confirmed that a sweat antigen can be detected by using the antibody according to the present invention.

Thus, according to the present invention, a subject (particularly, a subject highly sensitive to a sweat antigen) can be determined as being a patient with a sweat antigen-associated disease or having a risk of developing the sweat antigen-associated disease (particularly, having a risk of developing the sweat antigen-associated disease), by detecting the sweat antigen. According to the present invention, a therapeutic plan or preventive measure against the sweat antigen-associated disease, such as sweat antigen removal, can also be established, because the localization or distribution of a sweat antigen and its concentration in a subject (particularly, a subject highly sensitive to a sweat antigen) can be analyzed by detecting the sweat antigen on the surface of or within the body of the subject.

A biological sample from a human affected with a sweat antigen-associated disease or having a risk of being affected therewith contains a larger amount of IgE antibodies specific for a fraction with histamine releasing activity, than in normal humans. Thus, the presence of a sweat antigen-specific IgE antibody in a biological sample serves as an index of a sweat antigen-associated disease or a risk of development thereof. According to Examples 4 and 5, it was confirmed that a sweat antigen-specific IgE antibody can be detected by using the antibody of the first aspect according to the present invention.

Thus, according to the present invention, a subject can be determined as being a patient with a sweat antigen-associated disease or having a risk of developing the sweat antigen-associated disease, by detecting the sweat antigen-specific IgE antibody. According to the present invention, a subject can also be determined as being highly sensitive to a sweat antigen, by detecting the sweat antigen-specific IgE antibody and comparing it to a reference value.

The determination method according to the present invention can also be carried out by combining the detection of a sweat antigen and the detection of a sweat antigen-specific IgE antibody.

The detection means used in the present invention may be any method that can detect a sweat antigen and/or a sweat antigen-specific IgE antibody in a test sample, without particular limitations. Examples thereof include an antigen-antibody reaction method. For example, the detection of a sweat antigen can be carried out by: collecting a test sample from a mammal including a human affected with a sweat antigen-associated disease or having a risk of being affected therewith; contacting the collected sample with the antibody according to the present invention; and determining whether or not antigen-antibody reaction is detected. Moreover, the detection of a sweat antigen-specific IgE antibody can be carried out by: collecting a test sample from a mammal including a human affected with a sweat antigen-associated disease or having a risk of being affected therewith; contacting the collected sample with a sweat antigen and the antibody according to the present invention; and determining whether or not antigen-antibody reaction is detected.

The "test sample" can be obtained by collection from the surface of or within the body of a subject (test subject) targeted by detection. The "test sample" may be any sample containing or likely to contain a sweat antigen and/or a sweat antigen-specific IgE antibody, without particular limitations. Examples thereof include body fluids (e.g., urine, blood, plasma, and serum), secretions (e.g., sweat, nasal discharge, and tears), cells, tissues, organs, and cell cultures (including, e.g., culture supernatants) of a test subject. Blood or sweat is preferable. Alternatively, purified products, extracts, preparations, or the like derived from them may be used.

In the method of the first aspect according to the present invention, the detection of a sweat antigen using antigen-antibody reaction can be carried out, for example, by:
(a) contacting a test sample with the antibody according to the present invention; and
(b) detecting an antigen-antibody complex.

More specifically, it can be carried out by:
(a-1) contacting a test sample with the antibody of the first aspect according to the present invention; and/or
(a-2) contacting the test sample with the antibody of the second aspect according to the present invention; and
(b) detecting an antigen-antibody complex.

In the method of the second aspect according to the present invention, the detection of a sweat antigen-specific IgE antibody using antigen-antibody reaction can be carried out, for example, by:
(a') contacting a test sample with the antibody according to the present invention and a sweat antigen; and
(b') detecting an antigen-antibody complex.

More specifically, it can be carried out by:
(a'-1) contacting a test sample with a sweat antigen;
(a'-2) contacting a first antigen-antibody complex formed in (a'-1) with the antibody according to the present invention; and
(b'-1) detecting a second antigen-antibody complex formed in (a'-2).

Alternatively, it can be carried out by:
(a'-I) contacting the antibody according to the present invention with a sweat antigen;
(a'-II) contacting a first antigen-antibody complex formed in (a'-I) with a test sample; and
(b'-I) detecting a second antigen-antibody complex formed in (a'-II).

The method of detecting antigen-antibody reaction is well known to those skilled in the art. For example, the sweat antigen and/or the sweat antigen-specific IgE antibody in a test sample can be detected by an immunological method. When tissue preparations are used as biological samples, a usual immunohistological staining method or the like can be used. When body fluids or culture supernatants or the like are used as biological samples, ELISA, RIA, a sandwich method, a competition method, a plaque method, an agglutination reaction method, flow cytometry, western blotting, or the like can be used.

The immunohistological staining method can be performed by, for example, a direct method using a sweat antigen and a labeled antibody or an indirect method using a labeled antibody against the antibody. Labeling materials known in the art, such as fluorescent materials, radioactive materials, enzymes, metals, and dyes, can be used as labeling agents.

In the sandwich method, for example, the antibody according to the present invention can be immobilized on a solid phase such as a plate and used as a primary antibody. Alternatively, the antibody according to the present invention can also be labeled and used as a secondary antibody. Monoclonal antibodies can be used as both primary and secondary antibodies. Alternatively, one of them may be a polyclonal antibody.

In the ELISA, for example, when the sweat antigen-specific IgE antibody is detected, the antibody according to the present invention is immobilized on a solid phase, which can then be reacted with a sweat antigen and further reacted with the serum of an atopic dermatitis patient, followed by detection using anti-human IgE antibodies to thereby detect sweat antigen-specific IgE in the atopic dermatitis patient's serum. Alternatively, anti-IgE antibodies are immobilized on a solid phase such as a plate, which can then be reacted with the serum of an atopic dermatitis patient and further reacted with a sweat antigen, followed by detection using the antibody according to the present invention to thereby detect sweat antigen-specific IgE in the atopic dermatitis patient's serum. Sweat antigen-specific IgG can be detected by using anti-human IgG antibodies instead of anti-human IgE antibodies.

According to the method of the first aspect according to the present invention, a test subject (particularly, a test subject highly sensitive to a sweat antigen) from which the antigen-antibody complex has been detected can be diagnosed or determined as being a patient with a sweat antigen-associated disease or having a risk of developing the sweat antigen-associated disease, because the sweat antigen is evaluated to be detected therein. Particularly, it has been reported as to atopic dermatitis that approximately 80% of the patients have sweat allergy (Hide M, et al. Acta Derm Venereol 2002; 82; 335-340). Thus, according to the determination method according to the present invention, whether or not a subject displaying atopic dermatitis-like symptoms is a patient with atopic dermatitis caused by the sweat antigen can be determined advantageously with high precision.

According to the method of the second aspect according to the present invention, a test subject from which the antigen-antibody complex has been detected can be diagnosed or determined as being a patient with a sweat antigen-associated disease or having a risk of developing the sweat antigen-associated disease, because the sweat antigen-specific IgE antibody is evaluated to be detected therein. According to the method of the second aspect according to the present invention, the diagnosis or determination as being a patient with a sweat antigen-associated disease or having a risk of developing the sweat antigen-associated disease can be achieved advantageously based on whether or not the sweat antigen-specific IgE antibody is detected, independently of results of histamine release test.

According to the present invention, the detection of a sweat antigen-specific IgE antibody can be applied to biological detection by using the histamine release inhibiting effect of the antibody according to the present invention.

According to the present invention, the detection of a sweat antigen can be applied to the analysis of the localization or distribution of a sweat antigen by combining it with a method such as an immunohistochemical staining method.

According to the present invention, the detection of a sweat antigen may be quantitative detection or may be qualitative detection. The quantitative detection can be performed for the concentration of a sweat antigen composition present in a sample, for example, by preparing in advance a calibration curve as to the relationship between sweat antigen composition concentrations and detection results using a sweat antigen composition standard solution with a known concentration, and comparing detection results from a sample with an unknown sweat antigen composition concentration to the calibration curve.

According to the present invention, there is provided a method of detecting a sweat antigen and/or a sweat antigen-specific IgE antibody using the detection means used in the present invention.

[Use of Antibody and Pharmaceutical Composition]

Sweat Antigen-Associated Disease

The sweat of a human including a patient with a sweat antigen-associated disease such as allergic dermatitis is known to contain a sweat antigen. Upon crosslinking of receptors (IgE receptors) on the surface of white blood cells by the binding of antigens via IgE antibodies, chemical transmitters including histamine are released, causing allergy. Thus, if the release of chemical transmitters can be inhibited by inhibiting the binding between the antigen and IgE specific for the antigen, allergic diseases caused by these chemical transmitters can be alleviated, mitigated, or treated. As shown later in Examples, the antibody according to the present invention was confirmed to inhibit sweat antigen-induced histamine release from the basophiles of patients with atopic dermatitis (Example 2 and 6-4 of Example 6)). Thus, the antibody according to the present invention is useful in the prevention or treatment of a sweat antigen-associated disease.

The antibody according to the present invention is preferably the antibody of the first aspect according to the present invention.

The sweat antigen-associated disease means a disease induced by an antigenic substance contained in sweat. Examples thereof include atopic dermatitis, urticaria (e.g., cholinergic urticaria), miliaria, dyshidrosis, allergic rhinitis, allergic conjunctivitis, and asthma. Atopic dermatitis or urticaria is preferable.

In the present specification, the "prevention" means the reduction of a risk of development in a subject having a predisposition to the disease but being still free from the disease. In the present invention, examples of the subject targeted by the "prevention" include individuals displaying no symptoms (signs) of the sweat antigen-associated disease, wherein the concentration of a sweat antigen-specific IgE antibody in the serum is higher than the normal level or the presence of a sweat antigen is observed in the body fluid. Such a subject can be identified by the determination method or the like according to the present invention.

In the present specification, the "treatment" means any treatment of the disease in a patient, particularly, a human, and also encompasses the improvement or alleviation of symptoms of the disease. In this context, the phrase "improvement or alleviation of symptoms" means the mitigation of the severity of the sweat antigen-associated disease, i.e., the alteration of symptoms in a patient to a milder case. The alteration to a milder case is represented by clinical symptoms such as itching or eruption or by the reduction or absence of abnormal findings in clinical test using blood or skin tissues or the like as materials.

In the present invention, examples of the subject targeted by the "treatment" include individuals displaying symptoms (signs) of the sweat antigen-associated disease, wherein the concentration of a sweat antigen-specific IgE antibody in the serum is higher than the normal level or the presence of a sweat antigen is observed in the body fluid. Such a subject can also be identified by the determination method or the like according to the present invention.

In the present invention, examples of the "symptoms (signs) of the sweat antigen-associated disease" include: for atopic dermatitis, itching and aggravation of eruption after sweating; for urticaria, the occurrence of wheal, itching, or pain sensation caused by the stimulation of sweating resulting from rise in body heat, mental strain, or the like; for miliaria, erythema and papule; for dyshidrosis, palmoplantar blisters and desquamation; for allergic rhinitis, nasal discharge, sneeze, and nasal congestion; for allergic conjunctivitis, itching in eyelids or conjunctiva, hyperemia, and lacrimation; and for asthma, stridor, dyspnea, and coughing.

According to the present invention, there is provided use of the antibody according to the present invention for the production of a preventive or therapeutic agent for a sweat antigen-associated disease.

According to the present invention, there is provided a method of preventing or treating a sweat antigen-associated disease, comprising administering a preventively or therapeutically effective amount of the antibody according to the present invention to a mammal including a human.

Agent of Diagnosing Sweat Antigen-Associated Disease

As shown later in Examples, a sweat antigen composition can be detected using the antibody according to the present invention (Examples 3, 6, and 7). The presence of a sweat antigen in a biological sample serves as an index of a sweat antigen-associated disease or a risk of development thereof. Moreover, a sweat antigen composition-specific IgE antibody can be detected using the antibody according to the present invention (Examples 4 and 5). The presence of a sweat antigen-specific IgE antibody in a biological sample serves as an index of a sweat antigen-associated disease or a risk of development thereof. Thus, the antibody according to the present invention is useful in the diagnosis of a sweat antigen-associated disease or a risk of development thereof.

According to the present invention, there is provided a method of diagnosing a sweat antigen-associated disease or a risk of development thereof, comprising detecting a sweat antigen-specific IgE antibody in a biological sample using the antibody according to the present invention.

The diagnosis method according to the present invention can be carried out by: collecting a test sample from a mammal including a human affected with a sweat antigen-associated disease or having a risk of being affected therewith; contacting the collected sample with the antibody according to the present invention; and determining whether or not a sweat antigen and/or a sweat antigen-specific IgE antibody is detected. In the diagnosis method according to the present invention, the sweat antigen or the sweat antigen-specific IgE antibody can be detected according to the detection method according to the present invention. In the diagnosis method according to the present invention, determination (diagnosis) can be achieved according to the determination method according to the present invention.

Diagnosis Kit

According to the present invention, there is provided a kit of diagnosing a sweat antigen-associated disease or a risk of development thereof, comprising at least the antibody of the first aspect according to the present invention and/or the antibody of the second aspect according to the present invention.

According to the kit of the present invention, whether or not a subject is affected with a sweat antigen-associated disease can be diagnosed using, as an index, a sweat antigen and/or a sweat antigen-specific IgE antibody present in a biological sample. According to the kit of the present invention, whether or not a subject has a risk of developing the sweat antigen-associated disease can also be diagnosed using, as an index, a sweat antigen and/or a sweat antigen-specific IgE antibody present in a biological sample.

The antibody according to the present invention may be provided, for example, in a form dissolved in a solution or immobilized on a solid phase.

The antibody according to the present invention may be labeled with an enzyme or the like.

The kit according to the present invention detects the presence of a sweat antigen and/or a sweat antigen-specific IgE antibody by detecting antigen-antibody reaction.

Thus, the kit according to the present invention may contain, if desired, various reagents for carrying out antigen-antibody reaction, for example, primary and secondary antibodies, reaction buffers, washing solutions, reaction substrates, sweat antigen standard solutions, instructions, tools, etc.

Pharmaceutical Composition

A pharmaceutical composition according to the present invention comprises the antibody according to the present invention as an active ingredient and may be used preferably in a form of a composition containing the purified antibody and arbitrary ingredients, for example, saline, an aqueous glucose solution, or a phosphate buffer.

The antibody according to the present invention may be administered in any dosage form without particular limitations and can be administered through any administration route of oral and parenteral administrations (e.g., intravenous injection, intramuscular injection, hypodermic administration, rectal administration, transdermal administration, and local administration) to a mammal including a human. Parenteral administration, particularly, transdermal administration, is preferable.

Dosage forms for oral and parenteral administrations and preparation methods thereof are well known to those skilled in the art. These compositions can be prepared according to a standard method, for example, by mixing the antibody according to the present invention with a pharmaceutically acceptable carrier and so on.

For example, a substance that is routinely used in the pharmaceutical field and is unreactive to the antibody according to the present invention is used as the pharmaceutically acceptable carrier. For example, a stabilizer, an antiseptic, a tonicity agent, etc., usually used can be used as the pharmaceutically acceptable carrier.

Examples of the dosage forms for parenteral administration include injectable preparations (e.g., intravenous drip injections, intravenous injections, intramuscular injections, hypodermic injections, and intradermal injections), external preparations (e.g., poultices, sprays, aerosols, and liniments), suppositories inhalants, ophthalmic drugs, eye ointments, nasal drops, eardrops, and liposome preparations. External preparations are preferable.

The dose of the pharmaceutical composition differs depending on the age, body weight, sex, general health, and severity of disease of a patient, and the component of the antibody to be administered. For example, when the pharmaceutical composition according to the present invention is transdermally administered, the antibody can be administered at a daily dose of 0.01 to 5000 mg/kg (body weight), preferably 0.1 to 1000 mg/kg (body weight), per adult. The administration method actually used may drastically vary depending on the judgment of a clinician and may depart from this dose range.

The diagnosis agent according to the present invention can be prepared using any means appropriate for the purpose.

[Hybridoma Producing Sweat Antigen-Specific Antibody]

A hybridoma of the first aspect according to the present invention can produce the antibody of the first aspect according to the present invention.

According to the present invention, a hybridoma producing the antibody of interest can be selected from hybridomas obtained by the fusion between lymphocytes obtained by immunization with a sweat antigen composition and myeloma cells, using, as an index, an amount of histamine release from a sweat antigen stimulation-responsive cell.

The hybridoma of the first aspect according to the present invention can be screened by the screening method according to the present invention.

The hybridoma of the first aspect according to the present invention can be produced by the production method according to the present invention.

According to the present invention, there is provided a hybridoma (Mouse-Mouse hybridoma smith-1) deposited under accession No. FERM BP-11110 (transferred from FERM P-21439) with International Patent Organism Depositary, National Institute of Advanced Industrial Science and Technology (Central 6, Higashi 1-1-1, Tsukuba, Ibaraki, 305-8566 JAPAN) on Nov. 16, 2007.

Moreover, there is provided a hybridoma (Mouse-Mouse hybridoma smith-2) deposited under accession No. FERM BP-11111 (transferred from FERM P-21440) with International Patent Organism Depositary, National Institute of Advanced Industrial Science and Technology (Central 6, Higashi 1-1-1, Tsukuba, Ibaraki, 305-8566 JAPAN) on Nov. 16, 2007.

Furthermore, there is provided a hybridoma (Mouse-Mouse hybridoma smith-8) deposited under accession No. FERM BP-11112 (transferred from FERM P-21697) with International Patent Organism Depositary, National Institute of Advanced Industrial Science and Technology (Central 6, Higashi 1-1-1, Tsukuba, Ibaraki, 305-8566 JAPAN) on Oct. 1, 2008.

A hybridoma of the second aspect according to the present invention can produce the antibody of the second aspect according to the present invention.

According to the present invention, a hybridoma producing the antibody of interest can be selected from hybridomas obtained by the fusion between lymphocytes obtained by immunization with a sweat antigen composition and myeloma cells using, as an index, the binding ability of a sweat antigen composition binding to the antibody of the first aspect according to the present invention.

According to the present invention, there is provided a hybridoma (Mouse-Mouse hybridoma adam-1) deposited under accession No. FERM BP-11113 (transferred from FERM P-21696) with International Patent Organism Depositary, National Institute of Advanced Industrial Science and Technology (Central 6, Higashi 1-1-1, Tsukuba, Ibaraki, 305-8566 JAPAN) on Oct. 1, 2008.

According to the present invention, there are provided the following inventions:

(1) An antibody or a functional fragment thereof which can react with a sweat antigen composition and inhibit the histamine releasing activity of the composition on a sweat antigen stimulation-responsive cell.

(2) The antibody or the functional fragment thereof according to (1), wherein the antibody is obtained using, as an antigen, a fraction with histamine releasing activity contained in secretions from a human sweat gland.

(3) The antibody or the functional fragment thereof according to (1), wherein the antibody is obtained using, as an antigen, an anti-human cystatin A antibody-non-adsorbed fraction obtained by subjecting a fraction with histamine releasing activity contained in secretions from a human sweat gland to anti-human cystatin A antibody affinity chromatography.
(4) The antibody or the functional fragment thereof according to any one of (1) to (3), wherein the antibody is produced from a hybridoma screened using, as an index, an amount of histamine release from the sweat antigen stimulation-responsive cell.
(5) The antibody or the functional fragment thereof according to any one of (1) to (4), wherein the antibody is produced from a hybridoma deposited under FERM BP-11110 or FERM BP-11111.
(6) The antibody or the functional fragment thereof according to any one of (1) to (5), wherein the antibody is a monoclonal antibody.
(7) A method of determining a sweat antigen-associated disease or a risk of development thereof, comprising detecting a sweat antigen or a sweat antigen-specific IgE antibody in a test sample using an antibody according to any one of (1) to (6).
(8) The determination method according to (7), wherein the sweat antigen-associated disease is selected from the group consisting of atopic dermatitis, urticaria, miliaria, dyshidrosis, allergic rhinitis, allergic conjunctivitis, and asthma.
(9) A pharmaceutical composition for use in the prevention or treatment of a sweat antigen-associated disease, comprising an antibody or a functional fragment thereof according to any one of (1) to (6) and optionally one or more pharmaceutically acceptable carrier and/or diluent.
(10) The pharmaceutical composition according to (9), wherein the sweat antigen-associated disease is selected from the group consisting of atopic dermatitis, urticaria, miliaria, dyshidrosis, allergic rhinitis, allergic conjunctivitis, and asthma.
(11) An agent or kit of diagnosing a sweat antigen-associated disease, comprising an antibody or a functional fragment thereof according to any one of (1) to (6).
(12) The diagnosis agent or kit according to (11), wherein the sweat antigen-associated disease is selected from the group consisting of atopic dermatitis, urticaria, miliaria, dyshidrosis, allergic rhinitis, allergic conjunctivitis, and asthma.
(13) A hybridoma for use in the production of an antibody or a functional fragment thereof which can react with a sweat antigen composition and inhibit the histamine releasing activity of the composition on a sweat antigen stimulation-responsive cell, the hybridoma producing a sweat antigen-specific antibody and being obtained by selection with an amount of histamine release from the sweat antigen stimulation-responsive cell as an index.
(14) The hybridoma according to (13), wherein the hybridoma has been deposited under accession No. FERM BP-11110 or FERM BP-11111.
(15) A method of screening for a hybridoma producing a sweat antigen-specific antibody, comprising selecting a hybridoma producing an antibody having inhibiting effect on histamine releasing activity, using, as an index, an amount of histamine release from a sweat antigen stimulation-responsive cell.
(16) A method of producing a hybridoma producing a sweat antigen-specific antibody, comprising:
(i) selecting a hybridoma producing an antibody having inhibiting effect on histamine releasing activity, using, as an index, an amount of histamine release from a sweat antigen stimulation-responsive cell; and
(ii) cloning the hybridoma obtained in (i).

EXAMPLES

Hereinafter, the invention of this application will be described in more details and further specifically with reference to Examples. However, the invention of this application is not intended to be limited to the examples below.

Example 1

Preparation of Purified Fraction Non-Adsorbed on Anti-Human Cystatin A Column 1-1. Preparation of Concentrated Sweat Human sweat was passed through 100-μm and 70-μm mesh filters (Nylon Cell Strainer, BD Falcon) to remove insoluble matter. Then, precipitates were further removed using a 0.22-μm filter (Bottle Top Filter, 1 L, Corning Inc.). 4 L of the sweat thus filter-filtrated was concentrated into approximately 150 mL by ultrafiltration (3000 M.W. cut) and used as a material for sweat antigen purification.

1-2. Separation Using Anion-Exchange Column 75 mL of concentrated sweat adjusted to pH 8.0 was loaded onto an anion-exchange column MonoQ 10/100 GT (GE Healthcare Biosciences) equilibrated in advance with 10 mmol/L Tris-HCl (pH 8.0), followed by elution with an NaCl concentration gradient of 0 to 1.0 M in 10 mmol/L Tris-HCl (pH 8.0). AKTA explorer (GE Healthcare Biosciences) was used as a chromatographic apparatus for purification.

In order to select a fraction containing a substance inducing histamine releasing activity, histamine release test using the basophiles of atopic dermatitis patients was conducted on each fraction.

First, each appropriately diluted fraction was mixed at a 1:1 ratio with an atopic dermatitis patient-derived basophile fraction prepared into a HEPES buffer containing 5 mmol/L glucose, 0.03 w/v % HSA, 2 mmol/L $CaCl_2$, and 1 mmol/L $MgCl_2$, and incubated at 37° C. for 40 minutes. Supernatants and blood cell pellets were separated by centrifugation and separately denatured by the addition of 0.2 mol/L perchloric acid. Then, the concentration of histamine in supernatants obtained by centrifugation was measured by HPLC (Shimadzu LC solution). The ratio of the amount of histamine in the supernatants to the total amount of histamine was defined as histamine releasing activity.

In this context, the measurement of the amount of histamine was performed according to a method described in the document (Koro, O. et al., J. Allergy Clin. Immunol., 103, 663-670, 1999).

As a result, a fraction eluted in a salt concentration range of 0.25 to 0.3 mol/L NaCl, which had higher histamine releasing activity than in other fractions, was collected as a fraction exhibiting histamine releasing activity.

1-3. Separation Using Reverse-Phase Column 18 mL of the fraction obtained in Example 1-2 was diluted 10-fold with pure water and supplemented with TFA at a final concentration of 0.1 v/v %. This mixture was loaded onto a reverse-phase column (SOURCE 15 RPC ST 4.6/100 (GE Healthcare Biosciences), followed by elution with a concentration gradient from 0.1 v/v % TFA/distilled water to 0.1 v/v % TFA/acetonitrile. AKTA explorer (GE Healthcare Biosciences) was used as a chromatographic apparatus for purification.

After volatilization of TFA and acetonitrile, each eluted fraction was subjected to histamine release test in the same way as in Example 1-2.

As a result, an acetonitrile range of approximately 30 to 35 v/v %, which had higher histamine releasing activity than in other fractions, was collected as a fraction exhibiting histamine releasing activity (4 mL).

1-4. Separation by Gel Filtration Chromatography

The fraction obtained in Example 1-3 was freeze-dried, then dissolved again in PBS, and loaded onto Superdex 75 PC 3.2/30 (GE Healthcare Biosciences), followed by fractionation and elution with PBS (−). Smart system (GE Healthcare Biosciences) was used as a chromatographic apparatus for purification.

Each eluted fraction was subjected to histamine release test in the same way as in Example 1-2.

As a result, a fraction at an elution position ranging from 15 to 60 kD was collected as a fraction exhibiting histamine releasing activity (1.2 mL) and used as a QRX fraction in the subsequent procedures.

1-5. Removal of Cystatin A 1 mL to 0.9 mL of anti-human cystatin A antibodies (Biogenesis Ltd.) were dialyzed (3500 MWCO) against PBS (−). Then, the dialysate was added to 2 mL of NHS-activated Sepharose 4 Fast Flow (GE Healthcare Biosciences) gel and reacted with gentle stirring for 3 hours to prepare an anti-human cystatin A antibody-immobilized carrier. The procedures of antibody immobilization were performed according to the operation manual included therein. This affinity carrier was loaded onto a small column (1.8 mL) and washed/equilibrated with approximately 3-fold volume of PBS (−). Then, 0.5 mL of the fraction obtained in Example 1-4 was applied to the column, and a pass-through fraction was collected and used as the antigen fraction of interest.

In this context, it was confirmed by SDS-PAGE that most cystatin A was removed from the collected fraction.

Example 2

Preparation of Monoclonal Antibody 2-1. Immunization of Mice

The antigen fraction prepared in Example 1 was concentrated into 50 µL using a centrifugal concentrator (Pall Corp.; Nanosep; 3000 MWCO). A 20 µL aliquot thereof was mixed with the same amount of a Freund's complete adjuvant and injected for immunization to the hind footpads of 8-week-old female BALB/c mice. 7 and 19 days later, the mice were boosted with the same amount of the sweat antigen using a Freund's incomplete adjuvant. 3 days after the third booster, popliteal lymph nodes were collected and used as materials for cell fusion.

2-2. Cell Fusion

From the popliteal lymph nodes extirpated 3 days after the final immunization from the immunized mice, a suspension of lymph node cells was prepared using an RPMI medium. The obtained $9.9 \times 10^7$ cells were mixed with $1.98 \times 10^7$ mouse myeloma cells ($P_3U1$ strain) and centrifuged, followed by cell fusion using an electric cell fusion machine (Shimadzu Corp.; SSH-2 somatic Hybridizer, CCC-1 centrifugal cell compress). The cells thus fused were suspended in 420 mL of a complete RPMI medium (HAT medium) containing 10 v/v % fetal calf serum, 100 µmol/L hypoxanthine, 0.4 µmol/L aminopterin, and 16 µmol/L thymidine, then inoculated at a concentration of 0.2 mL/well to twenty-one 96-well micro-culture plates, and cultured at 37° C. in the presence of 5 v/v % $CO_2$. Hybridoma colonies appeared from all the wells within 10 days into the culture.

2-3. Selection of Hybridoma

The hybridomas in the culture wells were cultured in a complete RPMI medium, and the presence or absence of specific antibody production in the culture supernatants was detected as follows:

(1) IgG Assay in Hybridoma Culture Supernatant

50 µL of goat anti-mouse IgG antibodies (Sigma-Aldrich, Inc.; M4280) was added at a concentration of 4 µg/mL to each well of a 96-well micro-culture plate for assay and immobilized thereon. The wells were washed three times with a PBS (−) washing solution containing 0.05 v/v % Tween 20 and then blocked by the addition of 250 µL of 3 w/v % skim milk/PBS (−). To these wells, culture supernatants (50 µL) diluted 5-fold with 0.5 w/v % skim milk/PBS (−) were added for reaction. After washing, 50 µL of peroxidase-labeled goat anti-mouse IgG antibodies (Sigma-Aldrich, Inc.; A2554) diluted 5000-fold was added thereto and reacted with IgG bound with the wells. After washing, 100 µL of o-phenylenediamine (OPD)-$H_2O_2$ coloring solution (Wako Pure Chemical Industries, Ltd.) was added thereto and reacted for approximately 20 minutes. Absorbance at 490 nm was measured using a microplate reader.

(2) Determination of Inhibition of Histamine Releasing Activity

40 µL of culture supernatants in the wells confirmed to have IgG production (140 wells) was mixed with 10 µl of a 3000-fold dilution of the QRX fraction prepared in Example 1-4, and preincubated at 37° C. for 30 minutes. 50 µL of basophiles prepared from the peripheral blood of atopic dermatitis patients was added thereto. Histamine release test was conducted by the method described in Example 1-2.

As a result, the culture supernatants in 6 wells were confirmed to inhibit histamine release induced by the QRX fraction (FIG. 1).

The selected hybridomas were cloned by a limiting dilution method using BALB/c mouse thymocytes as feeder cells. The cloning procedures were performed at least twice or more. Antibodies produced from the obtained 6 hybridomas were designated as smith-1 to smith-6, respectively.

2-4. Purification of Monoclonal Antibody

The cells thus cloned were acclimatized to a serum-free medium (SFM) and then cultured at large scale using CEL-Line CL-350 (BD Biosciences) flasks. The obtained culture supernatants were applied to a centrifuge (10,000 RPM) to remove insoluble matter. The solution was then diluted 2-fold with PBS (−) and passed through Protein G-Sepharose 4 Fast Flow (GE Healthcare Biosciences) 2 mL column. The column was washed with PBS (−) as a washing solution until absorbance at OD 280 nm reached almost 0. Then, IgG was eluted using 0.2 mol/L Gly-HCl (pH 2.5). The concentration of proteins as IgG was calculated as to the obtained monoclonal antibodies from absorbance at 280 nm.

The purified antibodies (10 µg/mL) were examined for histamine releasing activity using the method described in Example 1-2.

Figure 2:
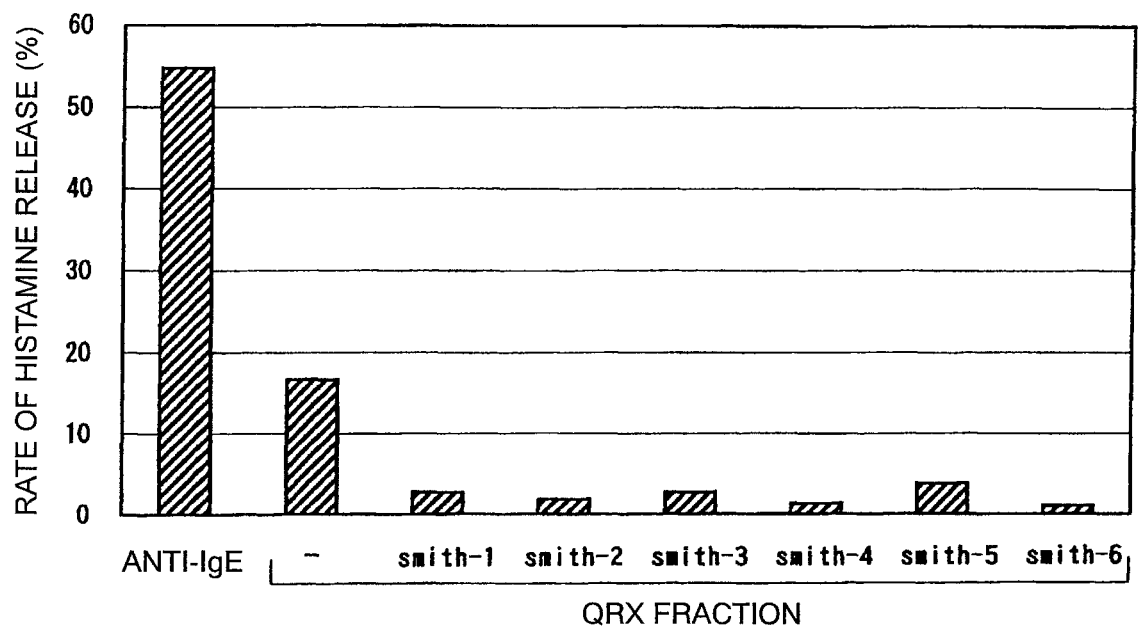
FIG. 2 is a diagram showing results of test on histamine release from patient-derived blood cells using purified hybridoma IgG.
Figure 2:
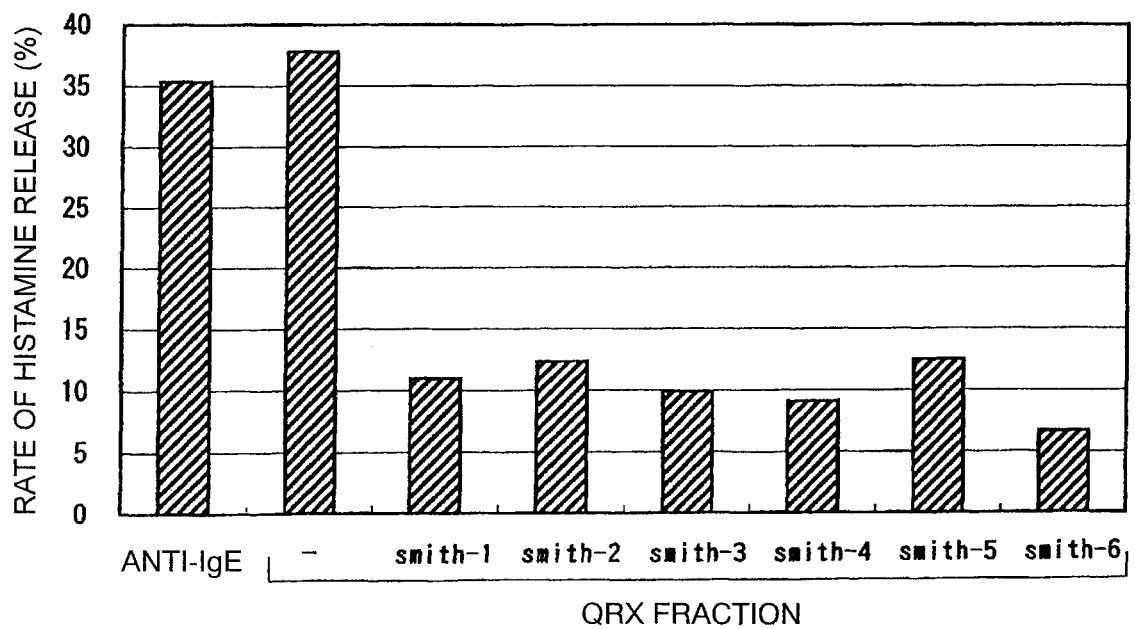

As a result, all the antibodies inhibited QRX fraction-induced histamine release from the basophiles of atopic dermatitis patients (patients A and B) (FIG. 2).

The obtained hybridomas were deposited under FERM BP-11110 or FERM BP-11111 with International Patent Organism Depositary, National Institute of Advanced Industrial Science and Technology.

Example 3

Reaction of QRX Fraction with Monoclonal Antibody 3-1. Purification of Sweat Antigen Using Monoclonal Antibody A substance having histamine releasing activity was purified from sweat antigen samples using a monoclonal antibody-immobilized affinity carrier.

The purified monoclonal antibodies (smith-1 to smith-6) were dialyzed (3500 MWCO) against PBS (−). Each antibody corresponding to 0.5 mg was added to 0.7 mL of NHS-activated Sepharose 4 Fast Flow (GE Healthcare Biosciences) gel and reacted with gentle stirring for 3 hours. The active groups were blocked by the addition of 0.1 mol/L Tris-HCl (pH 8.5) thereto. Then, the gel was washed with this buffer and 0.1 mol/L sodium acetate buffer (pH 4.5). This procedure was performed according to the operation manual included therein. Finally, the gel was washed/equilibrated with a sufficient amount of PBS (−) to prepare an anti-sweat antigen monoclonal antibody-immobilized carrier.

50 μL of this carrier was placed in a sample tube, to which the QRX fraction prepared in Example 1-4 was then added. The tube was shaken for 20 minutes and then centrifuged, and the obtained precipitates (antibody-immobilized carrier) were washed with PBS (−). Treatment in this cycle was performed three times with the amount of QRX increased to 4 μL, 20 μL, and 100 μL. The finally obtained precipitates were washed with a sufficient amount of PBS (−). Then, 120 μL of 0.1 mol/L Gly-HCl (pH 2.5) was added thereto, followed by elution procedures for 5 minutes. 100 μL of supernatants obtained by centrifuging this eluate was neutralized with a phosphate buffer, which was then replaced by PBS (−) using a desalting column (NAP-5; GE Healthcare Biosciences) equilibrated with PBS (−). Histamine releasing activity from the blood cells of atopic dermatitis patients was examined in the eluate thus prepared.

Figure 3:
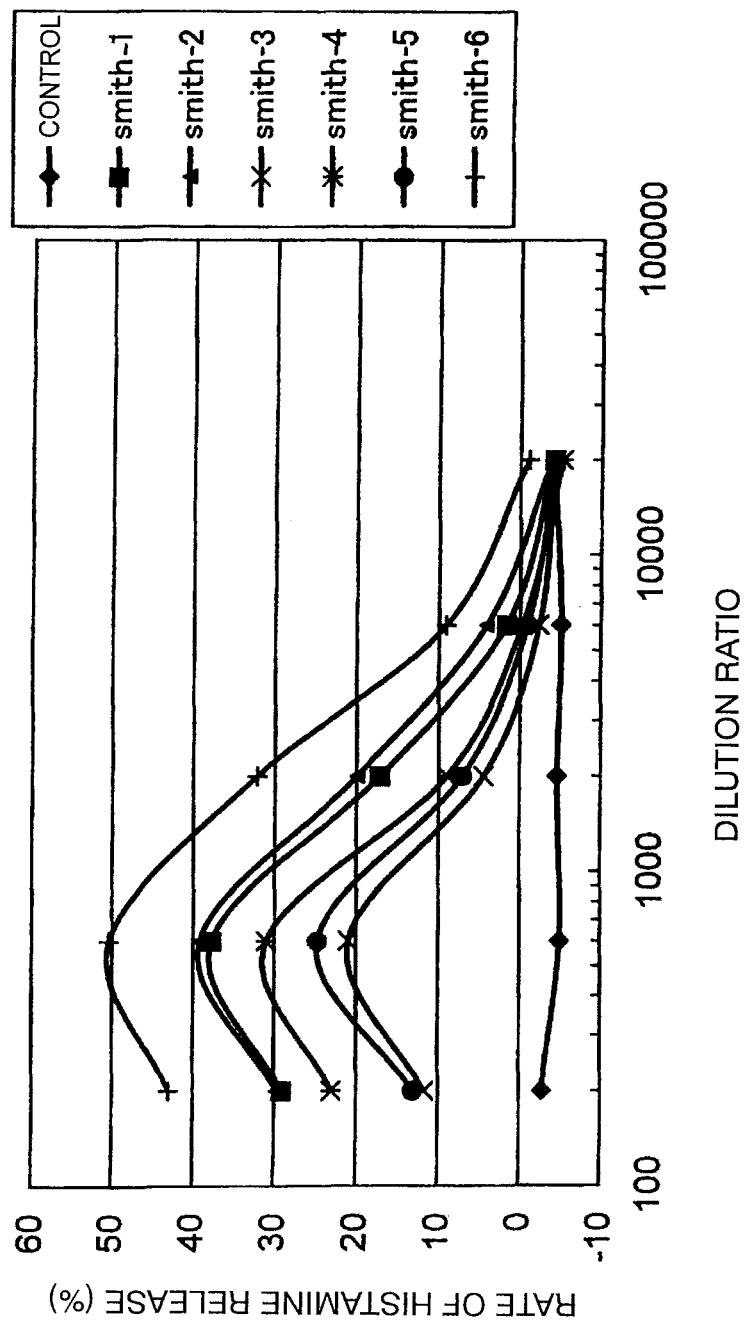
FIG. 3 is a diagram showing that a fraction having histamine releasing activity is collected using monoclonal antibodies obtained in Example 2.

As a result, histamine releasing activity was confirmed in the eluate even when any of the carriers were used. Thus, it was confirmed that a substance having histamine releasing activity can be collected using the monoclonal antibodies obtained in Example 2 (FIG. 3).

3-2. Detection of Sweat Antigen in Native-PAGE Gel Electrophoresis and Western Blotting The detection of sweat antigens was attempted by western blotting using the monoclonal antibodies obtained in Example 2.

10 μL of a QRX fraction concentrated 10-fold using a centrifugal concentrator (Pall Corp.; Nanosep; 3000 MWCO) was mixed with 5 μL of a sample buffer and 1 μL of 5 w/v % Coomassie Brilliant Blue G-250 (for native PAGE; Native PAGE sample preparation kit; manufactured by Invitrogen Corp.), and incubated at 85° C. for 10 minutes. Samples (corresponding to six lanes) treated in the same way as above were prepared and electrophoresed on a native polyacrylamide gel (NON-SDS-PAGE mini (4 to 20 w/v %) gel; manufactured by TEFCO). The gel after the electrophoresis was blotted to a nitrocellulose membrane (iBlot Gel Transfer Stacks Nitrocellulose, Regular: IB3010-01) by a usual method using Dry Blotting System (iBlot; manufactured by Invitrogen Corp.) The obtained membrane was blocked (room temperature, 2 hr) in 10 w/v % skim milk/PBS (−). This membrane was cut into strips corresponding to each lane, which were then respectively placed in the monoclonal antibody solutions (smith-1 to 6; 5 to 10 μg/mL) obtained in Example 2, and reacted overnight at 4° C. The strips were washed three times with T-TBS (TBS containing 0.05 v/v % Tween 20) and then reacted at room temperature for 2 hours with HRP-labeled anti-mouse IgG antibodies (MP Biomedicals, Inc.) diluted 2000-fold as secondary antibodies. After washing three times with T-TBS, bands were detected using an ECL luminescence detecting reagent (GE Healthcare Biosciences).

Figures 1, 4:
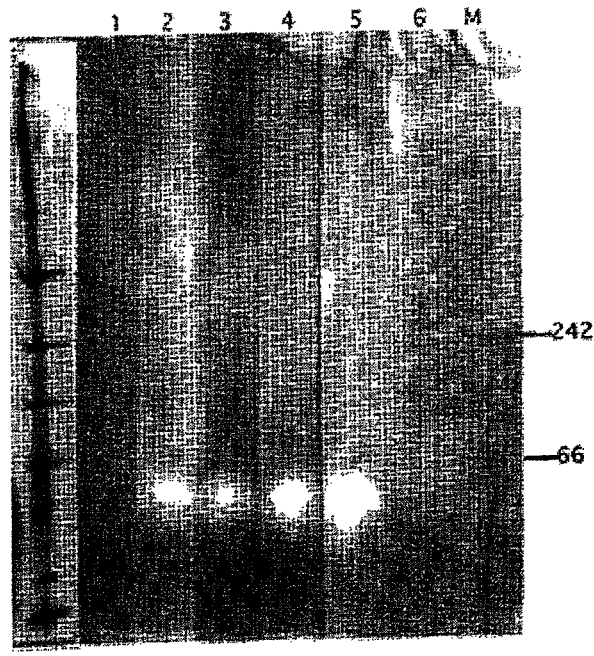
Figures 2, 4:
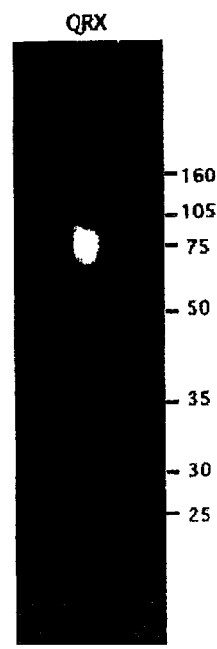
Figures 3, 4:
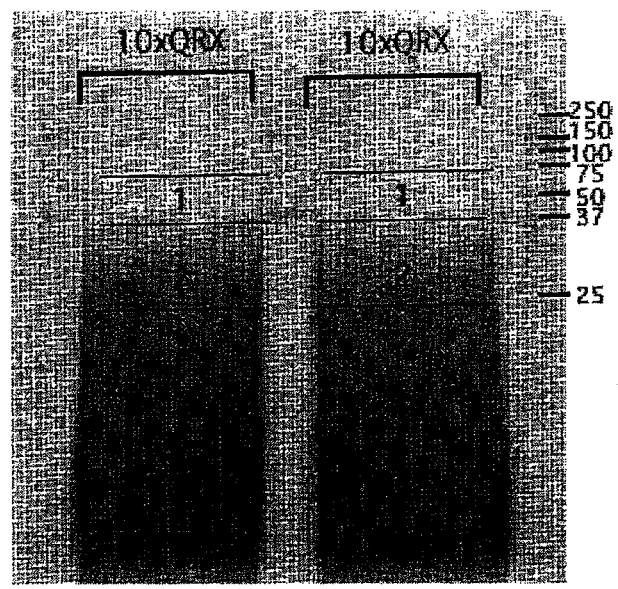
Figure 4:
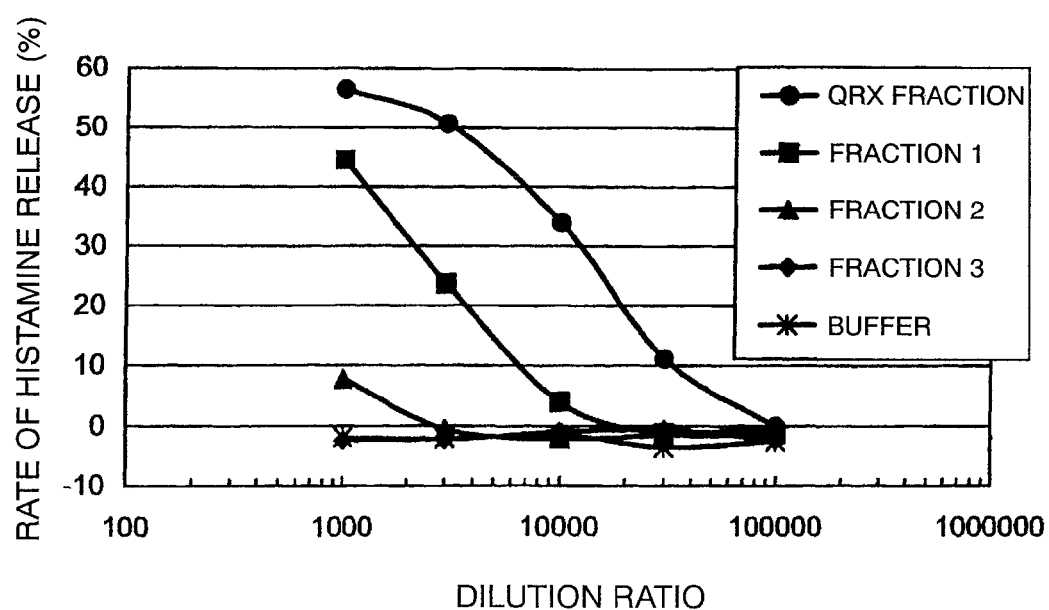

As a result, antigen bands were detected below the 66 kD position (position of the marker protein band) for smith-2, smith-3, smith-4, and smith-5, whereas no such bands were detected for smith-1 and smith-6 (FIG. 4-1).

Moreover, antigen detection was attempted by western blotting in the same way as above using native-PAGE gels (15 w/v % gels, PAGEL NPU-15L; manufactured by ATTO Corp.) differing in gel density. The antibody used was smith-2 (FIG. 4-2).

Subsequently, an antigen fraction having histamine releasing activity was examined for its distribution in native-PAGE electrophoresis. A QRX sample prepared by the same procedures as above was placed in 8 wells containing a native polyacrylamide gel (PAGEL NPU-15L; manufactured by ATTO Corp.) and electrophoresed (FIG. 4-3). After the electrophoresis, the gel was cut into three fractions (fractions 1 to 3) within the range shown in the diagram, which were then separately cut into narrower strips. Then, the strips were transferred to a dialysis tube (MWCO: 3000 daltons) and electrophoresed (100 V, 40 min.) in an electrophoretic buffer (25 mmol/L Tris/192 mmol/L glycine) for elution into the dialysis tube. The buffer in the eluate was replaced by PBS using a desalting column (NAP-10; GE Healthcare Biosciences). The antigen activity was determined by histamine release test.

As a result, histamine releasing activity was confirmed in the gel of fraction 1 at almost the same position as the band position detected in western blotting using the antibody smith-2 of the present invention (FIG. 4-4).

3-3. Detection of Sweat Antigen by ELISA Using Anti-Sweat Antigen Antibody (1) Preparation of Antiserum 40 μL of the QRX fraction was mixed with a Freund's complete adjuvant to prepare an emulsion, 10 μL of which was injected to each mouse footpad for immunization. Four immunizations were performed for 9 months in the same way as above, and blood was finally collected and used as antiserum.

(2) Preparation of F(ab')$_2$ Fragment of Smith-2

To 1 mL of smith-2 (1.5 mg/mL) dialyzed in 20 mmol/L sodium acetate buffer (pH 4.5), 0.25 mL of a 50 v/v % suspension of a pepsin-immobilized gel (manufactured by Pierce) washed with this buffer was added and reacted at 37° C. for 5 hours. After the reaction, supernatants were collected by centrifugation. The gel was resuspended by the addition of 200 μL of the same buffer as above and then centrifuged again to obtain approximately 1.1 mL of enzymatic digests combined with the obtained wash. pH was adjusted by the addition of 1.1 mL of 0.1 mol/L phosphate buffer (pH 7.8) containing 3 mol/L sodium chloride thereto. This solution was applied to a protein A column (GE Healthcare Biosciences) equilibrated with 0.05 mol/L phosphate buffer (pH 7.8) containing 1.5 M sodium chloride. The column was washed with 0.05 mol/L phosphate buffer (pH 7.8) containing 1.5 mol/L sodium chloride. 0.2 mot/L glycine-HCl buffer (pH 2.5) was used in elution. While the absorbance of the eluate was monitored at 280 nm, protein peaks of pass-through (and washed) portions were gathered and used as an F(ab')$_2$ fragment. It was confirmed by SDS polyacrylamide electrophoresis that the obtained F(ab')$_2$ fragment was free from undigested IgG.

(3) ELISA Test

50 μL of F(ab')$_2$ (1.5 μg/mL-PBS) was added to each well of a 96-well microplate for ELISA and immobilized on the well surface by leaving the plate standing at room temperature for 2 hours. After blocking with 3 w/v % BSA/PBS, 50 μL of a QRX fraction diluted with PBS to 4-fold dilution series was added thereto and reacted at room temperature for 2 hours. After washing with T-PBS (PBS (−) containing 0.05 v/v % Tween 20), 50 μL of the antiserum (diluted 75-fold/0.2 w/v % BSA/PBS) of the preceding paragraph (1) was added thereto and reacted at room temperature for 1 hour. After washing with T-PBS, 50 μL of peroxidase-labeled goat anti-mouse IgG (Fc specific: Sigma-Aldrich, Inc.) diluted 3000-fold with 0.2 w/v % BSA in PBS was added thereto and reacted at room temperature for 1 hour. After the reaction, the wells were washed with T-PBS, and 100 μL of o-phenylenediamine coloring reagent (manufactured by Wako Pure Chemical Industries, Ltd.) and hydrogen peroxide was injected thereto for color development. The color reaction was terminated by the injection/addition of 100 μL of 1 mol/L sulfuric acid. Then, the absorbance at 490 nm was measured using a microplate reader (Bio-Rad model Benchmark Plus, manufactured by Bio-Rad Laboratories, Inc.). The serum of unimmunized mice was used in a control experiment.

Figure 5:
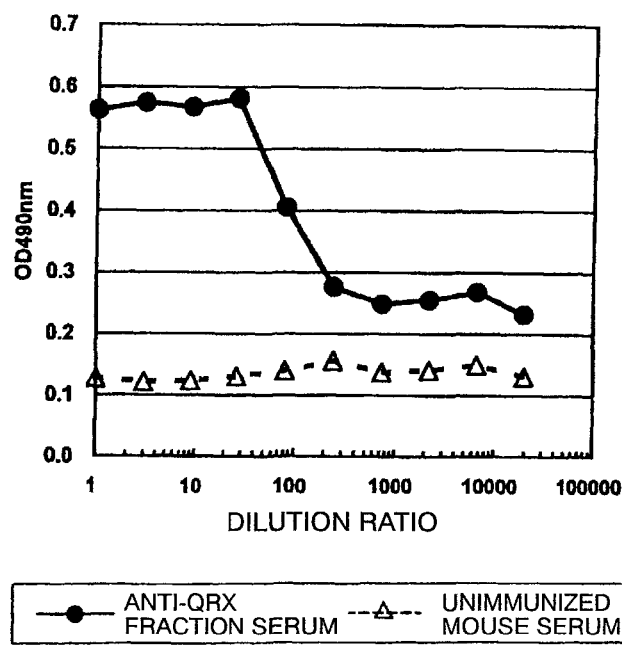
FIG. 5 is a diagram showing results of ELISA test.

As a result, it was confirmed that a sweat antigen can be detected specifically by sandwich ELISA using smith-2 F(ab')$_2$ in a solid phase (FIG. 5).

Example 4

Assay of Anti-Sweat Antigen Specific IgE Antibody in Patient's Serum (1)

It has been reported that sweat antigen-specific IgE antibodies are present in the serum of atopic dermatitis patients (Experimental Dermatology 15: 283-290, 2006). Thus, a method of diagnosing sweat allergy which comprises detecting sweat antigen-specific IgE antibodies in the serum of test subjects using the monoclonal antibody of the present invention was studied.

50 μL of the smith-2 antibody (2.5 μg/mL-PBS (−)) was added to each well of an ELISA plate and left standing overnight at 4° C. for immobilization. After blocking with 1 w/v % BSA-PBS (−), 50 μL of a QRX fraction diluted 50-fold was reacted therewith for immobilization through reaction with the immobilized antibody. After washing with T-PBS, 50 μL of test subject's serum (atopic dermatitis patient's or healthy individual's serum) diluted 10-fold with 1 w/v % BSA-PBS (−) was added thereto and reacted at room temperature for 90 minutes. After washing with T-PBS, 50 μL of peroxidase-labeled goat anti-human IgE antibodies (Bethyl Laboratories, Inc.) diluted 5000-fold with 0.2 w/v % BSA-PBS was added thereto and reacted at room temperature for 1 hour. After the reaction, the wells were washed with T-PBS, and 100 μL of o-phenylenediamine coloring reagent (manufactured by Wako Pure Chemical Industries, Ltd.) and hydrogen peroxide was injected thereto for color development. The color reaction was terminated by the injection/addition of 100 μL of 2 N sulfuric acid. Then, the absorbance at 490 nm was measured using a microplate reader (Bio-Rad model Benchmark Plus, manufactured by Bio-Rad Laboratories, Inc.).

Figure 6:
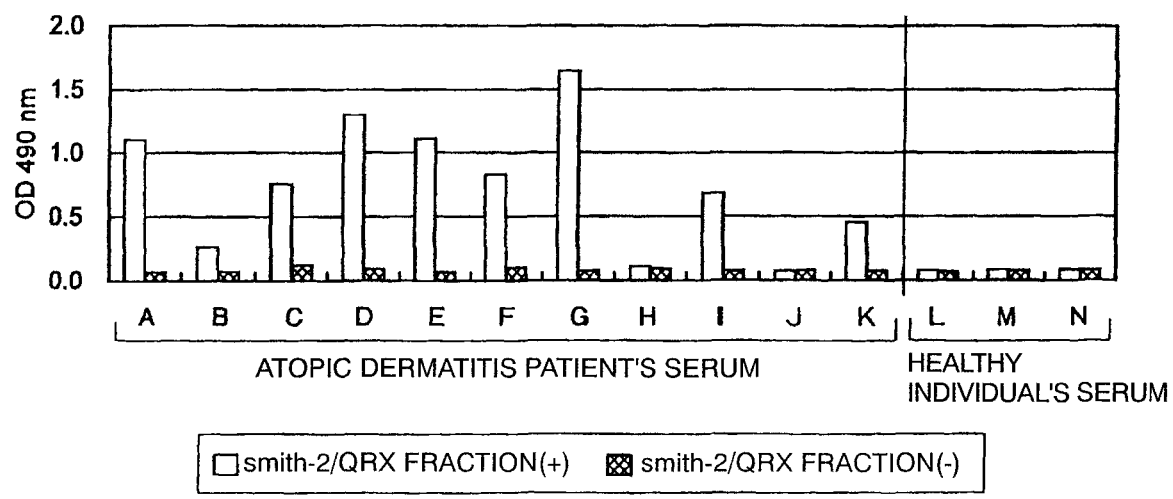
FIG. 6 is a diagram showing results of diagnosing atopic dermatitis using monoclonal antibodies obtained in Example 2.

As a result, anti-sweat antigen IgE antibodies were detected in 9 out of 11 atopic dermatitis patients (A to K), whereas the corresponding IgE was not observed in all of 3 healthy individuals (L to N) (FIG. 6). Use of this test method achieves test of sweat allergy using only a trace amount of serum even without performing histamine release test or the like (FIG. 6).

Example 5

Assay of Anti-Sweat Antigen Specific IgE Antibody in Patient's Serum (2)

Total IgE in serum was selectively collected and immobilized on an assay plate, with which the sweat antigen QRX fraction was then reacted. The monoclonal antibody of the present invention was further reacted with the QRX fraction to construct a system of detecting IgE specifically reacting with the sweat antigen.

50 μL of a goat anti-human IgE antibody (100-fold diluted) solution in a human IgE assay kit (Bethyl Laboratories, Inc.) was added to each well of an ELISA plate and immobilized by shaking at room temperature for 1 hour on a mixer. After blocking with 1 w/v % BSA-PBS (−), 50 μL of test subject's serum (atopic dermatitis patient's, cholinergic urticaria patient's, or healthy individual's serum) diluted 5-fold and 50-fold with 1 w/v % BSA-PBS (−) was added thereto and reacted at room temperature for 1 hour. After washing with T-PBS, 50 μL of a QRX fraction diluted 50-fold was reacted therewith. After washing with T-PBS, a biotin-labeled smith-2 antibody dilution prepared in Example 6-(1) at 5 μg/mL in 0.2 w/v % BSA-PBS was reacted therewith at room temperature for 1 hour. Subsequently, 50 μL of peroxidase-labeled streptavidin (Zymed Laboratories Inc.) diluted 1500-fold with 0.2 w/v % BSA-PBS was added thereto and reacted at room temperature for 1 hour. After the reaction, the wells were washed with T-PBS, and 100 μL of o-phenylenediamine coloring reagent (Wako Pure Chemical Industries, Ltd.) and hydrogen peroxide was added thereto for color development. The color reaction was terminated by the addition of 100 μL of 1 mol/L sulfuric acid. Then, the absorbance at 490 nm was measured using a microplate reader (Bio-Rad model Benchmark Plus, manufactured by Bio-Rad Laboratories, Inc.).

Figure 7:
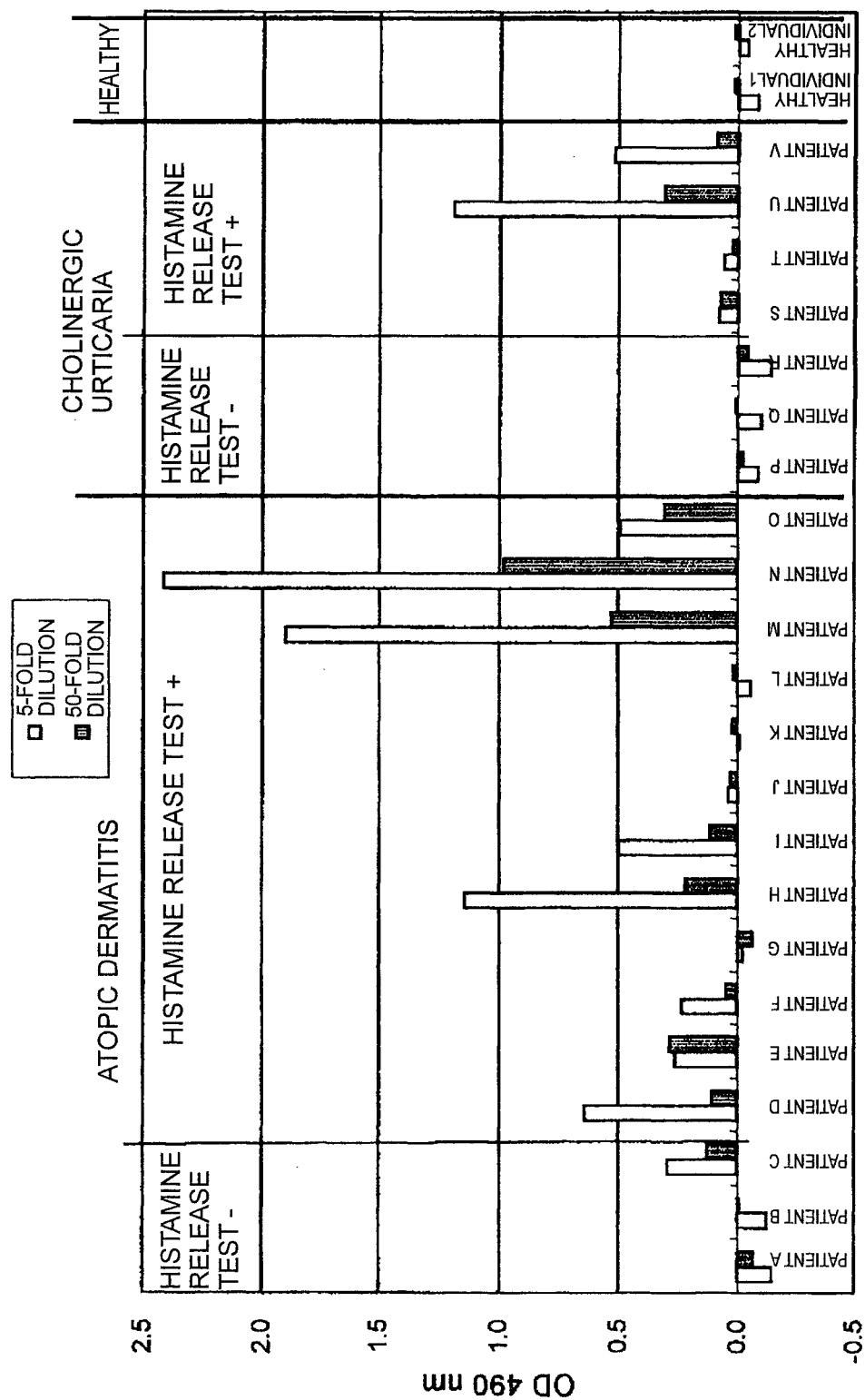
FIG. 7 is a diagram showing results of diagnosing sweat allergy by ELISA using anti-human IgE antibodies immobilized on a solid phase and a monoclonal antibody of the present invention as a labeled antibody.

As a result, sweat antigen-specific IgE was successfully detected without being influenced by IgG or the like (FIG. 7).

In this context, the patients A to C are atopic dermatitis patients. However, histamine release was not observed therein in histamine release test. Thus, they seem to be so-called nonresponders. However, since sweat antigen-specific IgE antibodies were confirmed in the serum of the patient C, the patient C can be determined as exhibiting hypersensitivity to the sweat antigen and developing atopic dermatitis or having exacerbated one, due to sweating or the like. Thus, the determination method according to the present invention can be used as an determination method substituting or complementing histamine release test.

Example 6

Preparation of Monoclonal Antibody Available in Sandwich ELISA 6-1. Immunization of Mice 500 μL of the QRX fraction prepared in Example 1-4 was concentrated into 50 μl using a centrifugal concentrator (Pall Corp.; Nanosep; 3000 MWCO). 10 μL of PBS (−) was added to a 15 μL aliquot thereof, and this mixture was mixed with 25 μL of an adjuvant TiterMAX Gold (TiterMAX) and injected for immunization to the hind footpads of 8-week-old female BALB/c mice. 15 days later, the mice were boosted in the same way as above. 3 days after this booster, popliteal lymph nodes were collected, and antibody-producing cells were selected using the smith-2 antibody and the QRX antigen.

6-2. Selection of Antibody-Producing Cell 6 wells of a 6-well plate for cell culture were washed with PBS (−). Then, 1.33 mL of the smith-2 F(ab')$_2$ fragment (10 μg/mL-PBS) solution prepared in Example 3-3 (2) was added to each well and gently stirred at 4° C. for 16 hours. The wells were washed with PBS (−) and subsequently with PBS (−) containing 1 v/v % FCS (fetal calf serum). Then, 1.33 mL of a QRX fraction diluted approximately 30-fold was added to each well and shaken at room temperature for 2 hours to immobilize the fraction thereon through reaction with the smith-2 F(ab')$_2$ fragment on the plate.

From the popliteal lymph nodes extirpated from the immunized mice, cells were prepared using PBS (−) containing 5 v/v % FCS (fetal calf serum). The cells were added at a concentration of $1.1 \times 10^7$ cells/1.33 mL per well to the plate. While the plate was gently stirred at intervals, the cells were reacted at room temperature for approximately 90 minutes. After the completion of the reaction, the plate surface was washed several times with PBS (−) containing 1 v/v % FCS (fetal calf serum) to remove non-adsorbed cells. Finally, 1.5 mL of a complete RPMI medium was added to each well, and the cells were cultured at 37° C. for 1 hour in the presence of 5 v/v % $CO_2$. Then, $7 \times 10^6$ cells adsorbed on the plate surface were collected using pipetting and rubber policeman.

6-3. Cell Fusion

Cell fusion was performed by the method described in Example 2-2 using the collected $7 \times 10^6$ cells and $1.75 \times 10^6$ mouse myeloma cells ($P_3U1$ strain). The cells thus fused were suspended in 20 mL of a complete RPMI medium containing 10 v/v % fetal calf serum and Briclone (Archport Ltd.) with a 10-fold diluted concentration as a final concentration, then inoculated at a concentration of 100 μL/well to 187-wells of 96-well micro-culture plates, and cultured at 37° C. in the presence of 5 v/v % $CO_2$. On the next day, the same amount of a complete RPMI medium containing HAT at a concentration twice the usual one per well was added thereto. Hybridoma colonies appeared from all the wells after 8 days into the culture.

6-4. Selection of Hybridoma

The hybridomas in the culture wells were cultured in a complete RPMI medium, and the presence or absence of specific antibody production in the culture supernatants was detected as follows:

(1) IgG Assay in Hybridoma Culture Supernatant

The amount of IgG in each well was measured according to the method described in Example 2-3, and wells confirmed to develop color of 0.5 or more in absorbance at 490 nm were selected.

(2) Selection of Monoclonal Antibody-Producing Cell by Sandwich ELISA Using Smith-2 F(ab')$_2$ Fragment and QRX Fraction 50 μL of the smith-2 F(ab')$_2$ fragment (5 μg/mL-PBS (−)) prepared by the method of Example 3-3 (2) was added to each well of an ELISA plate and left standing for 1 hour for immobilization. After blocking with 1 w/v % BSA-PBS (−), 50 μL of a QRX fraction diluted 25-fold was reacted therewith to immobilize QRX through reaction with the immobilized antibody. After washing with T-PBS, approximately 40 μL of culture supernatants in the wells confirmed in Example 6-4 (1) to have IgG production was added thereto and reacted for 1 hour. 50 μL of peroxidase-labeled goat anti-mouse IgG (Fc specific; Sigma-Aldrich, Inc.) diluted 2000-fold with PBS containing 0.2 w/v % BSA was added thereto and reacted at room temperature for 1 hour. After the reaction, the wells were washed with T-PBS, and 100 μL of o-phenylenediamine coloring reagent (Wako Pure Chemical Industries, Ltd.) and hydrogen peroxide was injected thereto for color development. The color reaction was terminated by the injection/addition of 100 μL of 2 N sulfuric acid. Then, the absorbance at 490 nm was measured using a microplate reader (Bio-Rad model Benchmark Plus, manufactured by Bio-Rad Laboratories, Inc.).

Figure 8:
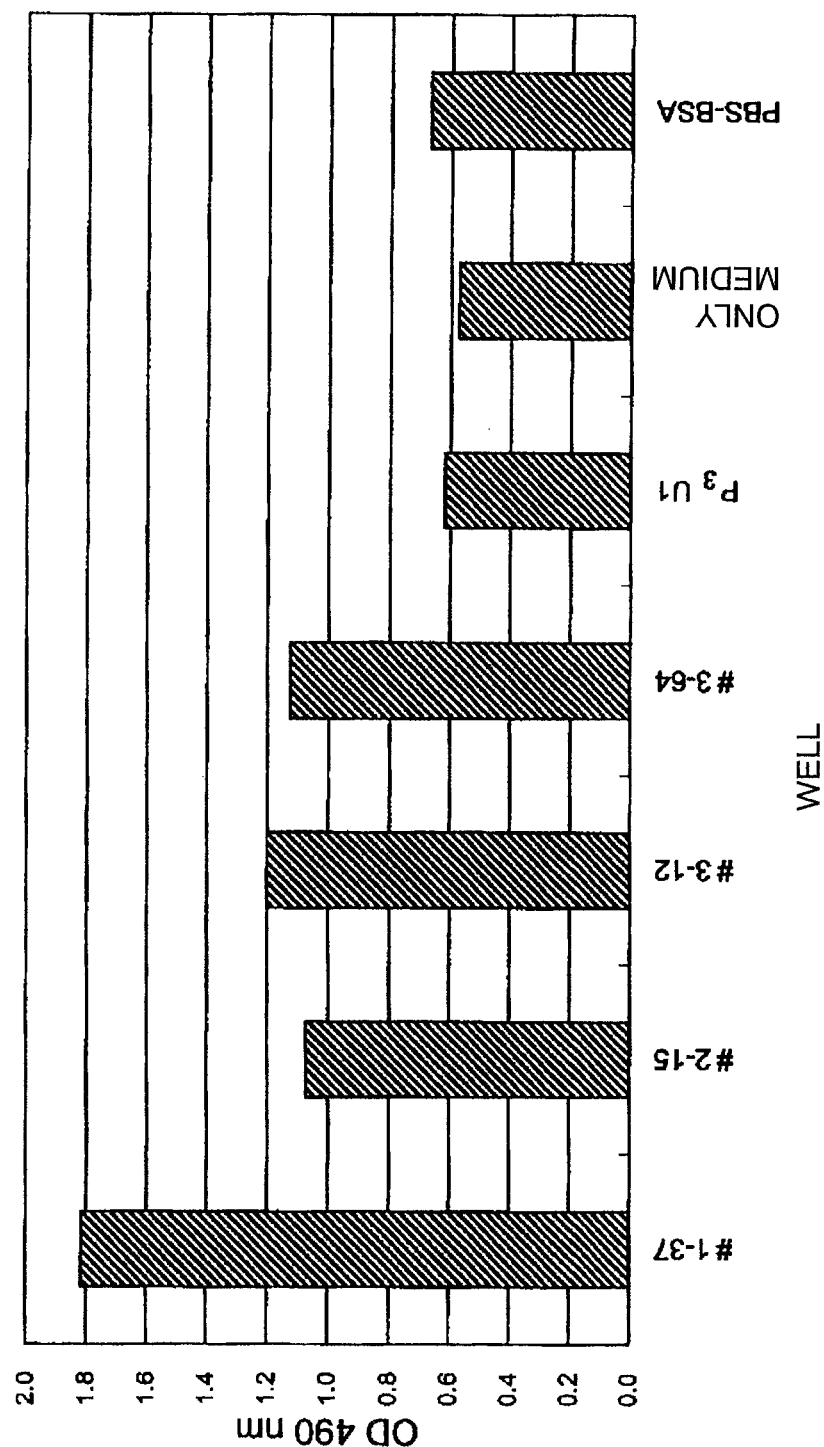
FIG. 8 is a diagram showing results of detecting monoclonal antibodies in hybridoma culture supernatants by sandwich ELISA test using immobilized smith-2F(ab')$_2$.

As a result, the culture supernatants in four wells (#1-37, #2-15, #3-12, and #3-64) were finally positive in this sandwich ELISA (FIG. 8). The hybridomas in the positive wells were cloned by a limiting dilution method using BALB/c mouse thymocytes as feeder cells. After the cloning, antibody-producing clones available in sandwich ELISA were obtained from the hybridomas derived from two wells by the same ELISA as above. Antibodies produced from these two hybridomas were designated as adam-1 and adam-2, respectively.

(3) Selection of Monoclonal Antibody-Producing Cell by Measurement of Histamine Release Inhibiting Activity 40 μL of culture supernatants in the wells confirmed in Example 6-4 (1) to have IgG production was mixed with 10 μL of a 3000-fold dilution of the QRX fraction, and preincubated at 37° C. for 30 minutes. 50 μL of a basophile solution prepared from the peripheral blood of atopic dermatitis patients was added thereto. The assay described in Example 2-3 (2) was carried out.

Figure 9:
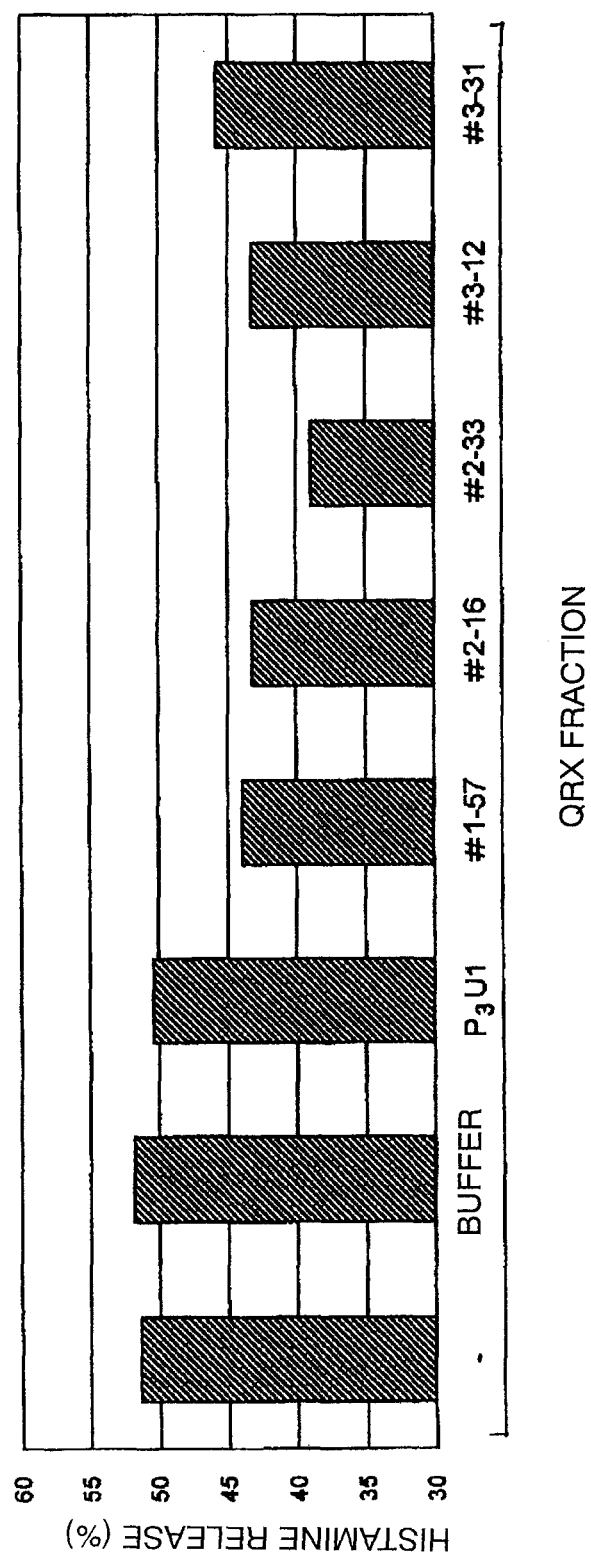
FIG. 9 is a diagram showing results of test on histamine release from patient-derived blood cells using hybridoma culture supernatants.

As a result, the culture supernatants in 5 wells (#1-57, #2-16, #2-33, #3-12, and #3-31) inhibited histamine release induced by the QRX fraction (FIG. 9). The hybridomas in these 5 wells were cloned by a limiting dilution method. Then, histamine release inhibiting activity was measured again. As a result, clones derived from three wells were finally obtained. Antibodies produced from these 3 hybridomas were designated as smith-7, smith-8, and smith-9, respectively.

(4) Properties of Monoclonal Antibody

The monoclonal antibodies adam-1 to 2 obtained in Example 6-4 (2) and the monoclonal antibodies smith-7 to 9 obtained in Example 6-4 (3) were purified by the method described in Example 2-4 and examined for their activities.

Each purified antibody (6.25 μg/mL) was subjected to sandwich ELISA using the method described in Example 6-4 (2).

Figure 10:
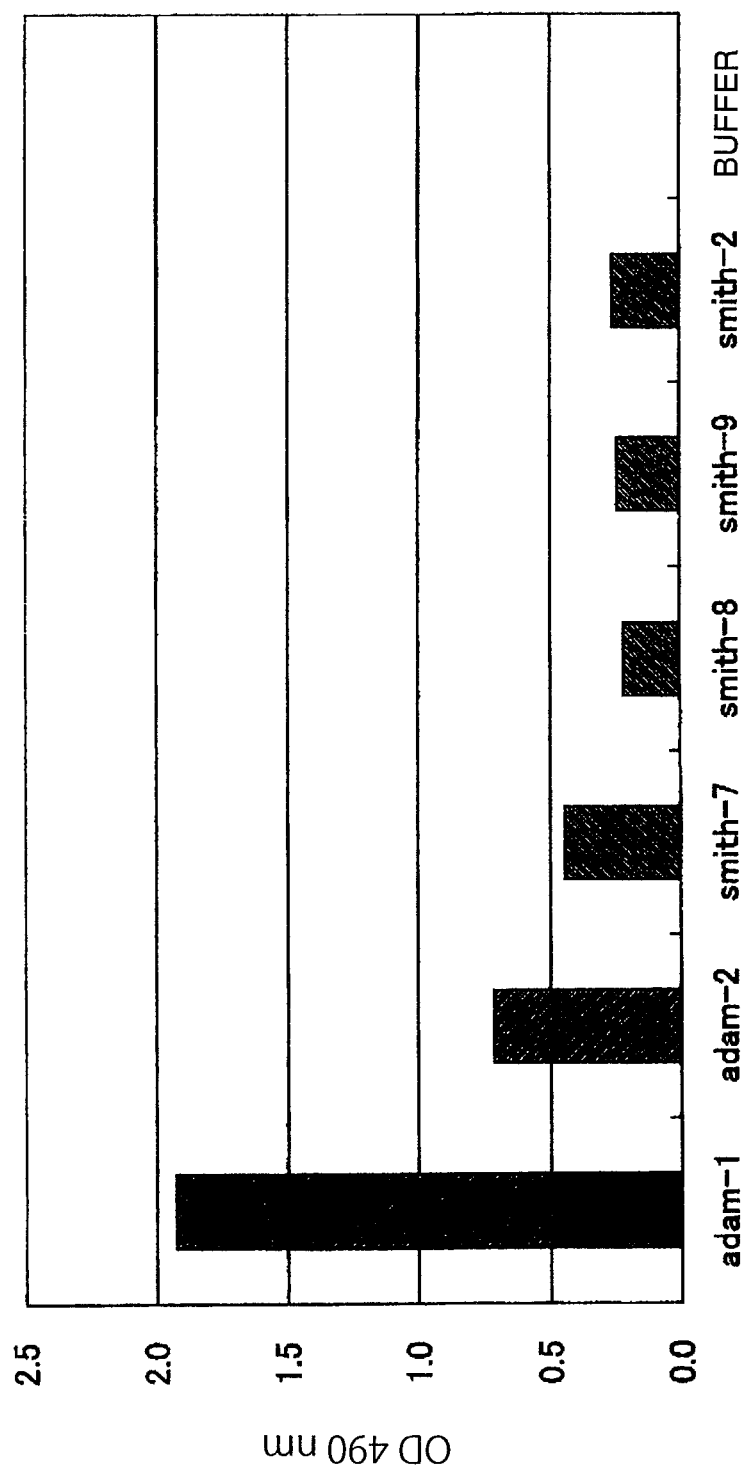
FIG. 10 is a diagram showing results of the reactivities of purified hybridoma monoclonal antibodies obtained in Example 6 in sandwich ELISA test using an immobilized smith-2F(ab')$_2$ fragment.

As a result, the adam-1 to 2 antibodies exhibited positive in sandwich ELISA (FIG. 10). This result demonstrated that the adam-1 to 2 antibodies can be combined with a smith-2 F(ab')$_2$ fragment in sweat antigen composition detection to detect a sweat antigen composition by a sandwich method. Moreover, the smith-7 to 9 antibodies also exhibited slightly positive in sandwich ELISA (FIG. 10). This result demonstrated that the smith-7 to 9 antibodies can be combined with a smith-2 F(ab')$_2$ fragment in sweat antigen composition detection to detect a sweat antigen composition by a sandwich method.

Next, purified antibodies prepared at a final concentration of 50, 10, or 2 μg/mL were used to examine histamine release inhibiting activity using the method described in Example 2-3 (2).

Figure 11:
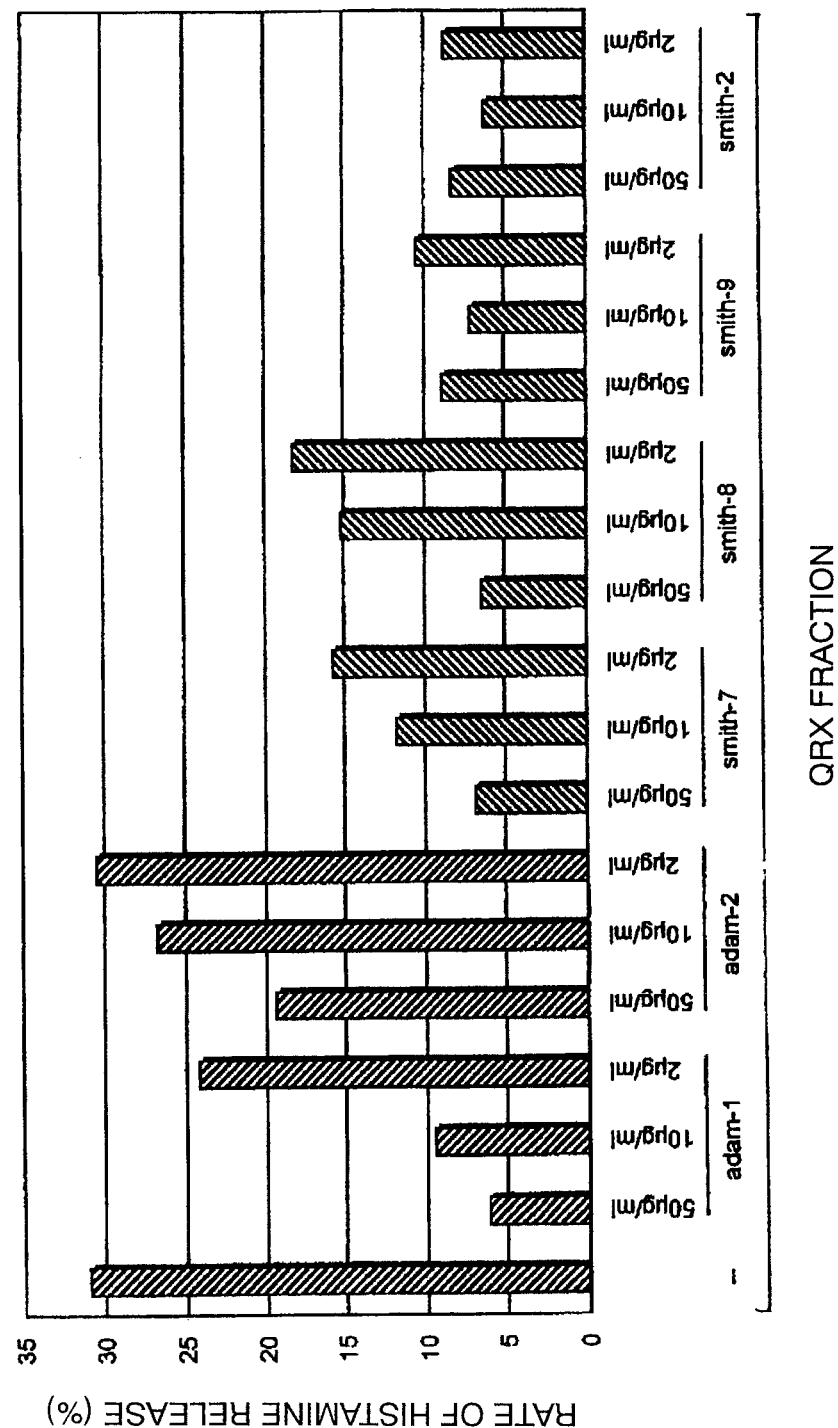
FIG. 11 is a diagram showing results of test on histamine release from patient-derived blood cells using purified hybridoma monoclonal antibodies obtained in Example 6.

As a result, all the monoclonal antibodies were confirmed to have dose-dependent histamine release inhibiting activity (FIG. 11). Moreover, these antibodies also produced the same results as above, albeit differing in the strength of release inhibiting activity, in histamine release test using the basophiles of two other atopic dermatitis patients.

Example 7

Detection of Sweat Antigen by ELISA Using Anti-Sweat Antigen Antibody

In Example 3-3, ELISA test for sweat antigen detection was conducted using the smith-2 F(ab')$_2$ fragment as an immobilized antibody and the serum of QRX antigen fraction-immunized mice as an antibody for sandwich. Thus, the construction of a more stable ELISA system was attempted by using the monoclonal antibodies prepared in Example 6-4 (2) instead of mouse serum.

(1) Preparation of Biotin-Labeled Monoclonal Antibody

The purified antibodies (adam-1 to 2 and smith-2 and 7 to 9) were separately prepared to 0.1 mg/0.2 mL with PBS (−). Sulfo-NHS-LC-Biotin (Pierce) was added thereto at a final concentration of 10 mmol/L and reacted at room temperature for 1 hour. The reaction was terminated by the addition of 2 μL of 1 mol/L monoethanolamine. Then, each reaction solution was applied to NAP-5 (GE Healthcare Biosciences) equilibrated with PBS (−) to remove the biotinylating reagent and so on.

(2) Construction of Sandwich ELISA System for Sweat Antigen Detection.

50 μL of each monoclonal antibody (adam-1 to 2 and smith-2 and 7 to 9; 5 μg/mL-PBS) was added to each well of a 96-well microplate for ELISA and immobilized on the well surface by leaving the plate standing at room temperature for 2 hours. After blocking with 1 w/v % BSA/PBS, 50 μL of a QRX fraction diluted 50-fold in PBS (−) was added thereto and reacted at room temperature for 1 hour. After washing with T-PBS (PBS (−) containing 0.05 v/v % Tween 20), 50 μL of each biotin-labeled monoclonal antibody (10 μg/mL-0.2 w/v % BSA/PBS) prepared in the preceding paragraph (1) was added thereto and reacted at room temperature for 1 hour. After washing with T-PBS, 50 μL of peroxidase-labeled streptavidin (Zymed Laboratories Inc.) diluted 1500-fold with PBS containing 0.2 w/v % BSA was added thereto and reacted at room temperature for 1 hour. After the reaction, the wells were washed with T-PBS, and 100 μL of o-phenylenediamine coloring reagent (Wako Pure Chemical Industries, Ltd.) and hydrogen peroxide was injected thereto for color development. The color reaction was terminated by the injection/addition of 100 μL of 1 mol/L sulfuric acid. Then, the absorbance at 490 nm was measured using a microplate reader (Bio-Rad model Benchmark Plus, manufactured by Bio-Rad Laboratories, Inc.).

Figures 1, 12:
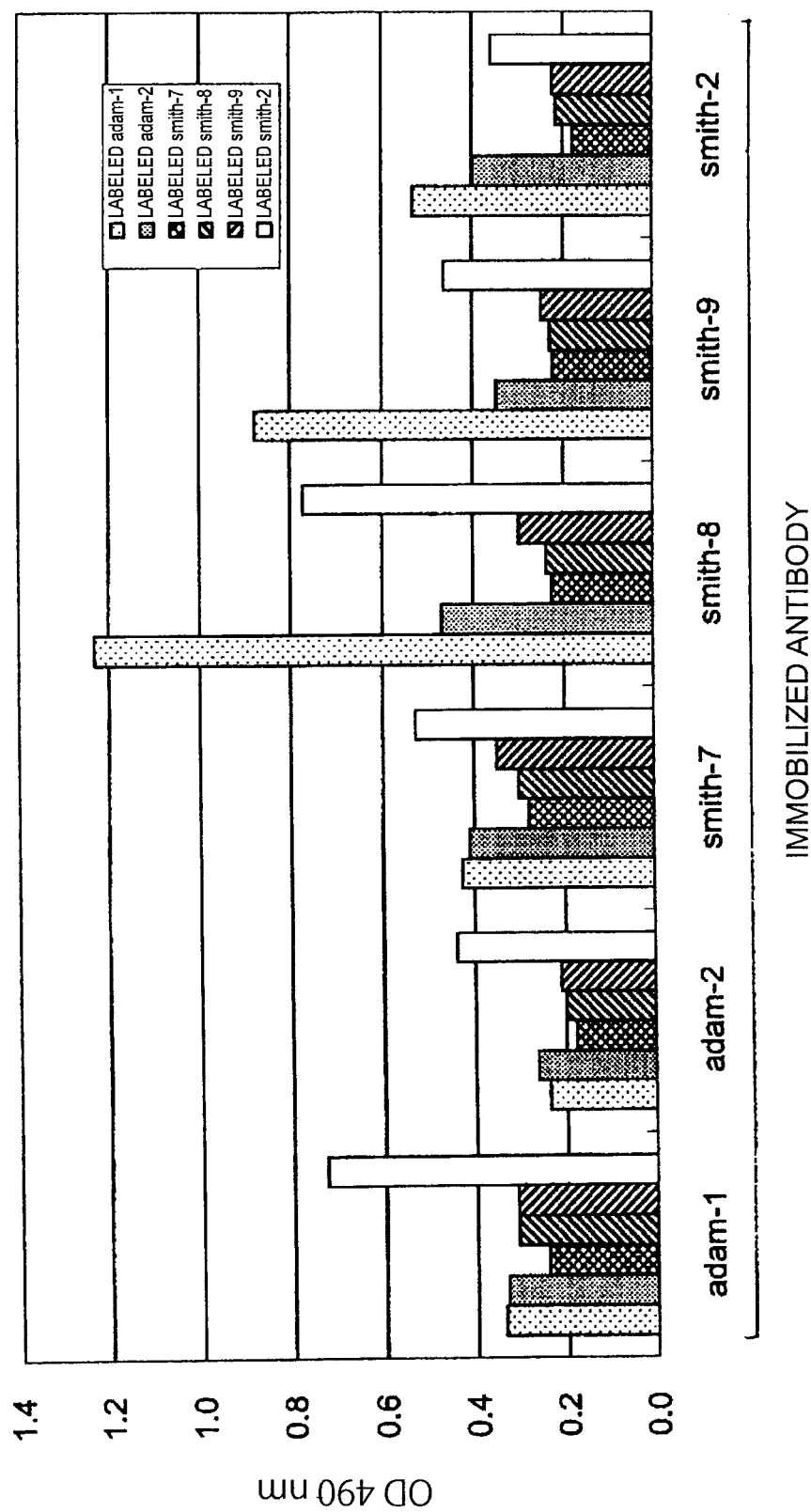
Figures 2, 12:
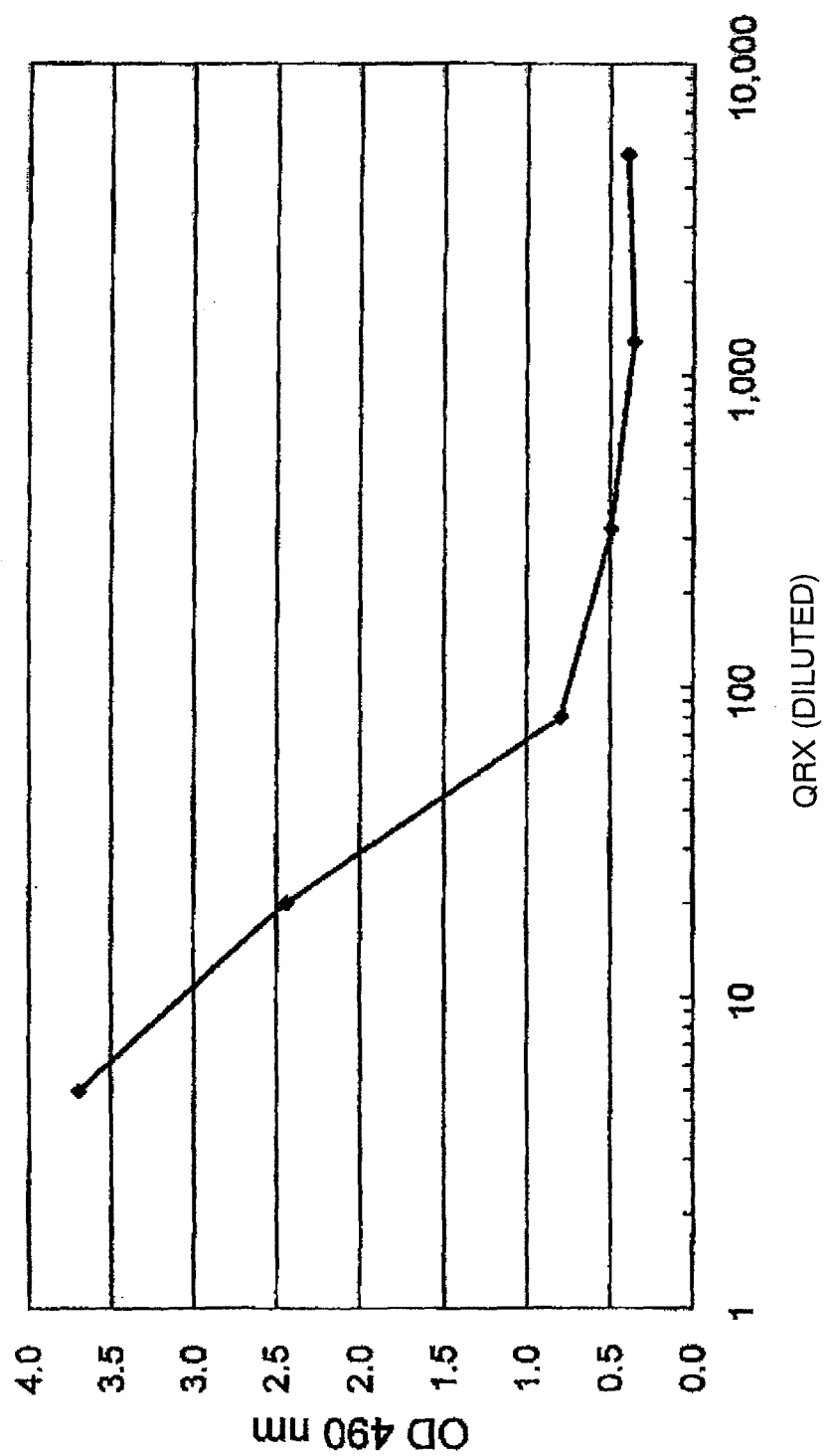

As a result, it was confirmed that a sweat antigen can be detected specifically using any combination (FIG. 12-1). It was confirmed that the sweat antigen can be detected with high sensitivity, particularly using the combinations immobilized smith-8-biotin-labeled adam-1, immobilized smith-9-biotin-labeled adam-1, immobilized adam-1-biotin-labeled smith-2, and immobilized smith-8-biotin-labeled smith-2 (FIG. 12-1). Among others, results of sweat antigen assay using the combination of smith-8 as an immobilized antibody and adam-1 as a biotin-labeled antibody are shown in FIG. 12-2.

Example 8

Assay of Anti-Sweat Antigen Specific IgE Antibody in Cholinergic Urticaria Patient's Serum As in atopic dermatitis patients, 60% or more of cholinergic urticaria patients contain sweat antigen-specific IgE antibodies in their serum (Takahagi S, et al., Br J Dermatol, 2008). Thus, a method of diagnosing sweat allergy which comprises detecting sweat antigen-specific IgE antibodies in the serum of test subjects using the monoclonal antibody according to the present invention was studied.

The same procedures as in the method described in Example 4 were performed.

50 μL of the smith-2 antibody (5 μg/mL-PBS (−)) was added to each well of an ELISA plate and left standing at room temperature for 2 hours for immobilization. After blocking with 1 w/v % BSA-PBS (−), 50 μL of a QRX fraction diluted 50-fold was added thereto and immobilized through reaction with the immobilized antibody with stirring for 1 hour on a mixer. After washing with T-PBS, 50 μL of test subject's serum (cholinergic urticaria patient's or healthy individual's serum) diluted 5-fold and 50-fold with 1 w/v % BSA-PBS (−) was added thereto and reacted at room temperature for 90 minutes. After washing with T-PBS, 50 μL of peroxidase-labeled goat anti-human IgE antibodies (Bethyl Laboratories, Inc.) diluted 5000-fold with 0.2 w/v % BSA-PBS was added thereto and reacted at room temperature for 1 hour. After the reaction, the wells were washed with T-PBS, and 100 μL of o-phenylenediamine coloring reagent (Wako Pure Chemical Industries, Ltd.) and hydrogen peroxide was injected thereto for color development. The color reaction was terminated by the injection/addition of 100 μL of 1 mol/L sulfuric acid. Then, the absorbance at 490 nm was measured using a microplate reader (Bio-Rad model Benchmark Plus, manufactured by Bio-Rad Laboratories, Inc.).

Figure 13:
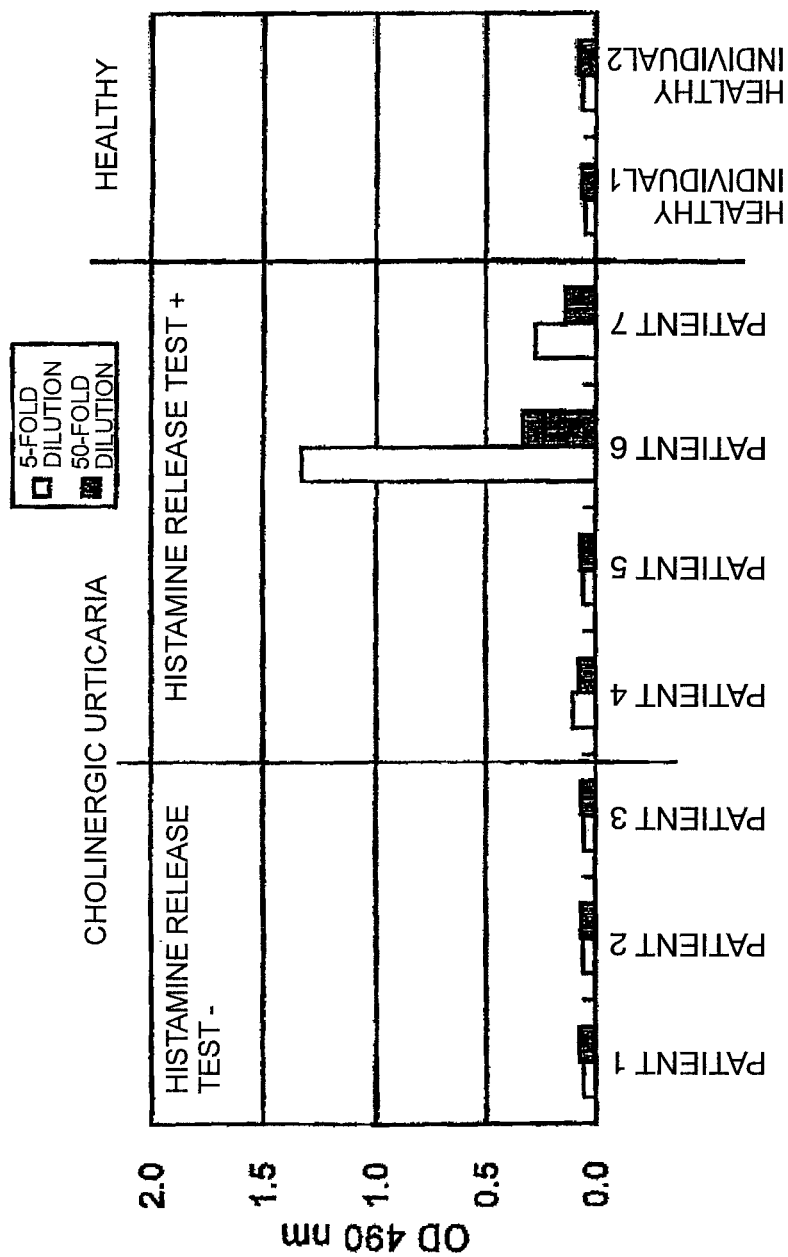
FIG. 13 is a diagram showing results of diagnosing sweat allergy in cholinergic urticaria patients using monoclonal antibodies obtained in Example 2.

As a result, anti-sweat antigen IgE antibodies were detected even in the cholinergic urticaria patients (patients 6 and 7). However, the corresponding IgE was not observed in the healthy individuals (FIG. 13). It was confirmed that use of this test method achieves test of sweat allergy in cholinergic urticaria patient using only a trace amount of serum even without performing histamine release test or the like.

The invention claimed is:

1. An antibody or a functional fragment thereof which reacts with a sweat antigen and inhibits histamine release in a sweat antigen-responsive cell, wherein said antibody is produced from a hybridoma deposited under accession No. FERM BP-11110, FERM BP-11111, or FERM BP-11112.

2. The antibody or the functional fragment thereof according to claim 1, wherein the antibody is produced from a hybridoma screened using, as an index, an amount of histamine release from the sweat antigen stimulation-responsive cell.

3. The antibody or the functional fragment thereof according to claim 1 or 2, wherein the antibody is a functional fragment of the antibody produced from the hybridoma deposited under accession No. FERM BP-11110, FERM BP-11111, or FERM BP-11112.

4. The antibody or functional fragment thereof according to claim 1, wherein the antibody or functional fragment thereof is produced from the hybridoma deposited under accession No. FERM BP-11110.

5. The antibody or functional fragment thereof according to claim 1, wherein the antibody or functional fragment thereof is produced from the hybridoma deposited under accession No. FERM BP-11111.

6. The antibody or functional fragment thereof according to claim 1, wherein the antibody or functional fragment thereof is produced from the hybridoma deposited under accession No. FERM BP-11112.

7. The antibody or the functional fragment thereof according to any one of claims 1 and 2 wherein the antibody is a monoclonal antibody.

8. An antibody or a functional fragment thereof which reacts with a sweat antigen, wherein said antibody is produced from a hybridoma deposited under accession No. FERM BP-11113.

9. The antibody or the functional fragment thereof according to claim 8, wherein the antibody is a monoclonal antibody.

10. The antibody or the functional fragment thereof according to claim 8, wherein the antibody is a functional fragment of the antibody produced from the hybridoma deposited under accession No. FERM BP-11113.

11. A pharmaceutical composition for use in the treatment of a sweat antigen-associated disease, comprising an antibody or a functional fragment thereof according to claim 1 and optionally one or more pharmaceutically acceptable carrier and/or diluent.

12. The pharmaceutical composition according to claim 11, wherein the sweat antigen-associated disease is selected from the group consisting of atopic dermatitis, urticaria, dyshidrosis, allergic rhinitis, allergic conjunctivitis, and asthma.

13. A pharmaceutical composition for use in the treatment of a sweat antigen-associated disease, comprising an antibody or a functional fragment thereof according to claim 2 and optionally one or more pharmaceutically acceptable carrier and/or diluent.

14. The pharmaceutical composition according to claim 13, wherein the sweat antigen-associated disease is selected from the group consisting of atopic dermatitis, urticaria, dyshidrosis, allergic rhinitis, allergic conjunctivitis, and asthma.

15. A pharmaceutical composition for use in the treatment of a sweat antigen-associated disease, comprising an antibody or a functional fragment thereof according to claim 8 and optionally one or more pharmaceutically acceptable carrier and/or diluent.

16. The pharmaceutical composition according to claim 15, wherein the sweat antigen-associated disease is selected from the group consisting of atopic dermatitis, urticaria, dyshidrosis, allergic rhinitis, allergic conjunctivitis, and asthma.

17. A hybridoma producing an antibody or a functional fragment thereof according to claim 1 or 2.

18. The hybridoma according to claim 17, which is deposited under accession No. FERM BP-11110.

19. The hybridoma according to claim 17, which is deposited under accession No. FERM BP-11111.

20. The hybridoma according to claim 17, which is deposited under accession No. FERM BP-11112.

21. A hybridoma which produces an antibody as set forth in claim 8.

22. The hybridoma according to claim 21, which is deposited under accession No. FERM BP-11113.

23. An agent or kit for determining a sweat antigen-associated disease or a risk of development thereof, comprising the antibody or a functional fragment thereof according to claim 1 or 2.

24. The agent or kit according to claim 23, wherein the sweat antigen-associated disease is selected from the group consisting of atopic dermatitis, urticaria, dyshidrosis, allergic rhinitis, allergic conjunctivitis, and asthma.

25. The agent or kit of claim 19, further comprising the antibody or a functional fragment thereof according to claim 8.

26. An agent or kit for determining a sweat antigen-associated disease or a risk of development thereof, comprising the antibody or a functional fragment thereof according to claim 8.

27. A method of determining a sweat antigen-associated disease or a risk of development thereof, comprising contacting a test sample with an antibody or fragment thereof as set forth in claim 1 or claim 2 and detecting the binding of the antibody or fragment and the sample.

28. The method according to claim 27, further comprising contacting the test sample with an antibody produced from a hybridoma deposited under accession No. FERM BP-11113, or a functional fragment thereof.

29. The method according to claim 27, wherein the sweat-antigen associated disease is selected from the group consisting of atopic dermatitis, urticaria, malaria, dyshidrosis, allergic rhinitis, allergic conjunctivitis, and asthma.

* * * * *

UNITED STATES PATENT AND TRADEMARK OFFICE
CERTIFICATE OF CORRECTION

| | | |
|---|---|---|
| PATENT NO. | : 8,546,542 B2 | Page 1 of 1 |
| APPLICATION NO. | : 12/990775 | |
| DATED | : October 1, 2013 | |
| INVENTOR(S) | : Michihiro Hide et al. | |

It is certified that error appears in the above-identified patent and that said Letters Patent is hereby corrected as shown below:

In the Claims

Column 30, Claim 25, Line 21, replace "kit of claim 19" with --kit of claim 23--.

Signed and Sealed this
Twenty-fifth Day of February, 2014

Michelle K. Lee
*Deputy Director of the United States Patent and Trademark Office*